United States Patent
Ding et al.

(10) Patent No.: US 9,815,753 B2
(45) Date of Patent: Nov. 14, 2017

(54) SUPPORTED METAL OXIDES FOR OLEFIN METATHESIS AND RELATED METHODS

(71) Applicant: Northwestern University, Evanston, IL (US)

(72) Inventors: Kunlun Ding, Evanston, IL (US); Peter C. Stair, Northbrook, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/853,017

(22) Filed: Sep. 14, 2015

(65) Prior Publication Data
US 2016/0075617 A1    Mar. 17, 2016

Related U.S. Application Data

(60) Provisional application No. 62/050,467, filed on Sep. 15, 2014.

(51) Int. Cl.
*C07C 6/04* (2006.01)
*B01J 31/40* (2006.01)
(Continued)

(52) U.S. Cl.
CPC ............... *C07C 6/04* (2013.01); *B01J 21/08* (2013.01); *B01J 23/28* (2013.01); *B01J 23/30* (2013.01);
(Continued)

(58) Field of Classification Search
CPC ............................... C07C 6/04; B01J 31/4015
See application file for complete search history.

(56) References Cited

U.S. PATENT DOCUMENTS 3,725,496 A * 4/1973 Kobylinski .............. B01J 37/00
585/643
3,952,070 A * 4/1976 Nowak .................... C07C 6/04
502/31
(Continued)

FOREIGN PATENT DOCUMENTS

| EP | 1473083 | 1/2004 |
|---|---|---|
| WO | WO/2004/016351 | 2/2004 |
| WO | WO/2009/013964 | 1/2009 |

OTHER PUBLICATIONS

Kazuhiko Amakawa et al., In Situ Generation of Active Sites in Olefin Metathesis, J. Am. Chem. Soc. 134, 2012, pp.11462-11473.
(Continued)

*Primary Examiner* — Sharon Pregler
*Assistant Examiner* — Alyssa L Cepluch
(74) *Attorney, Agent, or Firm* — Bell & Manning, LLC

(57) ABSTRACT

A method is provided comprising exposing a supported heterogeneous metathesis catalyst to an olefin compound for an activation time at an activation temperature; exposing the activated supported heterogeneous metathesis catalyst to a reactant capable of undergoing a metathesis reaction for a reaction time at a reaction temperature to produce metathesis products; and exposing the deactivated supported heterogeneous metathesis catalyst to a regenerating compound for a regeneration time at a regeneration temperature. The activity of the regenerated supported heterogeneous metathesis catalyst may be substantially the same or greater than the activity of the activated supported heterogeneous metathesis catalyst prior to deactivation. The activation temperature may be greater than the reaction temperature. The regenerating compound may be a second olefin compound or an inert gas.

20 Claims, 25 Drawing Sheets

(51) Int. Cl.
*B01J 38/04* (2006.01)
*B01J 21/08* (2006.01)
*B01J 23/28* (2006.01)
*B01J 23/30* (2006.01)
*B01J 23/92* (2006.01)
*B01J 37/03* (2006.01)
*B01J 27/188* (2006.01)
*B01J 35/00* (2006.01)
*B01J 35/10* (2006.01)

(52) U.S. Cl.
CPC ............ *B01J 23/92* (2013.01); *B01J 31/4015* (2013.01); *B01J 38/04* (2013.01); *B01J 27/188* (2013.01); *B01J 35/002* (2013.01); *B01J 35/1047* (2013.01); *B01J 37/036* (2013.01); *C07C 2521/08* (2013.01); *C07C 2523/20* (2013.01); *C07C 2523/28* (2013.01); *C07C 2523/30* (2013.01); *C07C 2523/36* (2013.01); *C07C 2523/46* (2013.01); *Y02P 20/52* (2015.11); *Y02P 20/584* (2015.11)

(56) References Cited

U.S. PATENT DOCUMENTS

| | | | |
|---|---|---|---|
| 4,709,115 A * | 11/1987 | Jung | ............................ C07C 6/04 585/643 |
| 7,371,917 B2 | 5/2008 | Schubert | |
| 7,754,647 B2 | 7/2010 | Schubert | |
| 2003/0028063 A1* | 2/2003 | Gartside | .................. B01J 21/08 585/646 |
| 2006/0183627 A1* | 8/2006 | Stephan | ................... B01J 23/92 502/38 |
| 2010/0167911 A1 | 7/2010 | Shum | |
| 2010/0191030 A1 | 7/2010 | Ikenaga | |

OTHER PUBLICATIONS

Kunlun Ding et al., Easily Regenerated High Performance Olefin Metathesis Catalysts, Abstract for Catalysis at the Confluence of Science and Technology, Conference in Pittsburgh, PA, Jun. 14-19, 2015.
Soe Lwin et al., Olefin Metathesis by Supported Metal Oxide Catalysts, ACS Catal. 4, 2014, pp. 2505-2520.

\* cited by examiner

SUPPORTED METAL OXIDES FOR OLEFIN METATHESIS AND RELATED METHODS

CROSS-REFERENCE TO RELATED APPLICATIONS

The present application claims priority to U.S. Provisional Patent Application No. 62/050,467 that was filed Sep. 15, 2014, the entire contents of which are hereby incorporated by reference.

REFERENCE TO GOVERNMENT RIGHTS

This invention was made with government support under grant number CHE1058835 awarded by the National Science Foundation. The government has certain rights in the invention.

BACKGROUND

Catalytic olefin metathesis has been blossoming for half century because of its unparalleled importance in the synthesis of many petrochemicals, fine chemicals and polymers. (See, A. H. Hoveyda, A. R. Zhugralin, *Nature* 450, 243 (2007) and J. C. Mol, P. W. N. M. van Leeuwen, in *Handbook of Heterogeneous Catalysis*. (2008), vol. 14, pp. 3240-3256.) Compared to the rapidly growing homogeneous olefin metathesis catalyst family, less progress has been achieved in the heterogeneous system, which is of greater interest to industrial applications in terms of cost. Tremendous efforts have been devoted to the developing more efficient and robust catalysts that could bridge the gap between the highly active homogeneous catalysts (Turnover frequency of $10^3$-$10^4$/h, TOF) and the easily separable heterogeneous catalysts (TOF of $10^1$-$10^2$/h). (See, C. Coperet, M. Chabanas, R. P. Saint-Arroman, J. M. Basset, *Angew. Chem. Int. Ed.* 42, 156 (2003); N. Popoff, E. Mazoyer, J. Pelletier, R. M. Gauvin, M. Taoufik, *Chem. Soc. Rev.* 42, 9035 (2013) and C. Coperet, *Dalton Trans.*, 5498 (2007).) One approach is heterogenizing homogeneous olefin metathesis catalysts by grafting them on various supports. This technique improves the recyclability of these expensive organometallic compounds at the expense of catalytic activities. (See, C. Coperet, M. Chabanas, R. P. Saint-Arroman, J. M. Basset, *Angew. Chem. Int. Ed.* 42, 156 (2003); N. Popoff, E. Mazoyer, J. Pelletier, R. M. Gauvin, M. Taoufik, *Chem. Soc. Rev.* 42, 9035 (2013) and C. Coperet, *Dalton Trans.*, 5498 (2007).) Another approach is promoting the activity of supported metal oxides, by means of using promoters such as organotin compounds, or rather peculiar and complicated pretreatment schemes. (See, Y. Iwasawa, H. Ichinose, S. Ogasawara, M. Soma, J. Chem. Soc., *Faraday Trans.* 77, 1763 (1981); B. N. Shelimov, I. V. Elev, V. B. Kazansky, *J. Catal.* 98, 70 (1986) and M. Kazuta, K. I. Tanaka, J. Chem. Soc., *Chem. Commun.*, 616 (1987).)

These catalysts on the one hand suffer from their synthetic complexities, on the other hand are nonregenerable after being deactivated under the reaction conditions. These two facts make these catalysts less affordable for large scale applications.

SUMMARY

Methods of making activated supported heterogeneous metathesis catalysts and methods of using the activated supported heterogeneous metathesis catalysts are provided. Also provided are methods of regenerating deactivated supported heterogeneous metathesis catalysts.

In one aspect a method is provided comprising exposing a supported heterogeneous metathesis catalyst comprising a support material and transition metal active groups dispersed on the support material to a first olefin compound for an activation time at an activation temperature, thereby providing an activated supported heterogeneous metathesis catalyst; exposing the activated supported heterogeneous metathesis catalyst to a reactant capable of undergoing a metathesis reaction for a reaction time at a reaction temperature to produce metathesis products, thereby providing a deactivated supported heterogeneous metathesis catalyst; and exposing the deactivated supported heterogeneous metathesis catalyst to a regenerating compound for a regeneration time at a regeneration temperature, thereby providing a regenerated supported heterogeneous metathesis catalyst. The activity of the regenerated supported heterogeneous metathesis catalyst may be substantially the same or greater than the activity of the activated supported heterogeneous metathesis catalyst prior to deactivation. The activation temperature may be greater than the reaction temperature. The regenerating compound may be a second olefin compound or an inert gas. The transition metal active groups may be transition metal oxide active groups.

In another aspect, a method of regenerating a deactivated supported heterogeneous metathesis catalyst is provided, the method comprising exposing a deactivated supported heterogeneous metathesis catalyst comprising a support material and transition metal active groups dispersed on the support material to an inert gas atmosphere substantially free of oxygen or air for a regeneration time at a regeneration temperature, thereby providing a regenerated supported heterogeneous metathesis catalyst. The activity of the regenerated supported heterogeneous metathesis catalyst may be substantially the same or greater than the activity of the supported heterogeneous metathesis catalyst prior to deactivation. The transition metal active groups may be transition metal oxide active groups.

Other principal features and advantages of the subject matter will become apparent to those skilled in the art upon review of the following drawings, the detailed description, and the appended claims.

BRIEF DESCRIPTION OF THE DRAWINGS

Illustrative embodiments of the subject matter will hereafter be described with reference to the accompanying drawings, wherein like numerals denote like elements.

FIGS. 2A and 2B shows on-line GC analysis and FIGS. 2C and 2D show MS analysis of the gaseous products generated during the propylene activation process as described in FIGS. 1C and 1D. FIGS. 2A and 2C are the results for $MoO_3$/$SiO_2$ and FIGS. 2B and 2D are the results for $WO_3$/$SiO_2$. UV-Raman spectra of $MoO_3$/$SiO_2$ and $WO_3$/$SiO_2$ are shown in FIGS. 2E and 2F, before and after the propylene activation process. FIG. 2G illustrates the propylene activation mechanism.

FIG. 3A shows the TPD-MS of $MoO_3$/$SiO_2$ after it was deactivated in propylene metathesis. FIG. 3B shows possible metallacyclobutane structures on the surface of activated $MoO_3$/$SiO_2$. FIG. 3C illustrates the mechanism of olefin metathesis and deactivation and regeneration of the catalyst. FIG. 3D shows the propylene metathesis activity of $MoO_3$/$SiO_2$ recovered at different temperatures. The catalyst was deactivated in propylene metathesis at 100° C. for 1 h. Regeneration conditions: 20 sccm $N_2$; 30° C./min from 20° C. to the target temperature and kept for 10 min.

FIG. 8A shows the $MoO_3$ loading dependent active site fraction and surface concentration from $^{13}CH_2$=$^{13}CH_2$ titration. FIG. 8B shows infrared and FIG. 8C shows UV resonance Raman spectra of $MoO_3$/$SiO_2$ with different loadings. FIG. 8D shows the $MoO_3$ loading dependent Raman band areas of monomeric and polymeric molybdate dioxo species. The infrared spectra are normalized by the amount of $SiO_2$. The Raman spectra are normalized by the intensity of Si—O vibrations (400-700 cm$^{-1}$). The Raman band areas in FIG. 8D are normalized by the surface areas of each $MoO_3$/$SiO_2$.

Figure 8A:
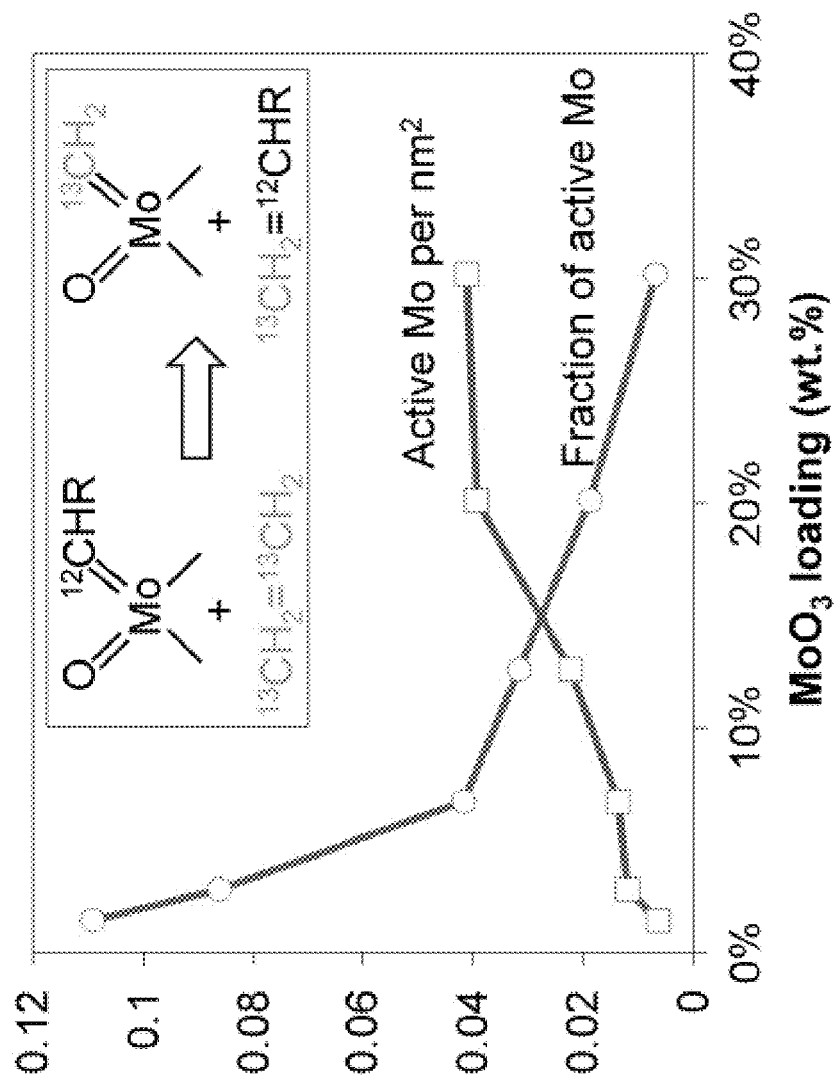
FIGS. 8A-8D relate to olefin metathesis active site counting and structure identification in $MoO_3$/$SiO_2$.
Figure 8B:
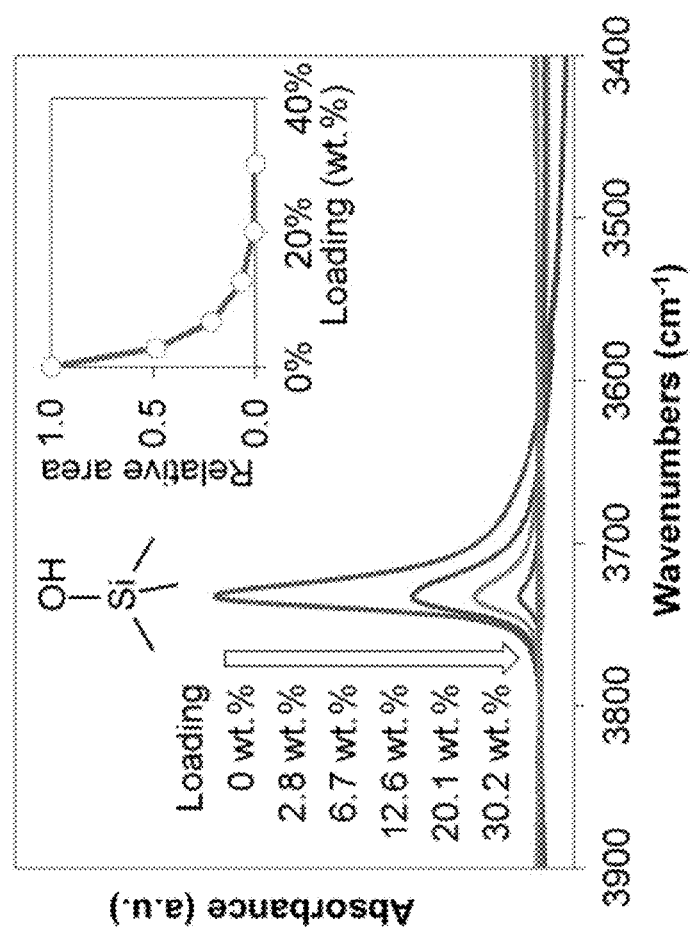
Figure 8C:
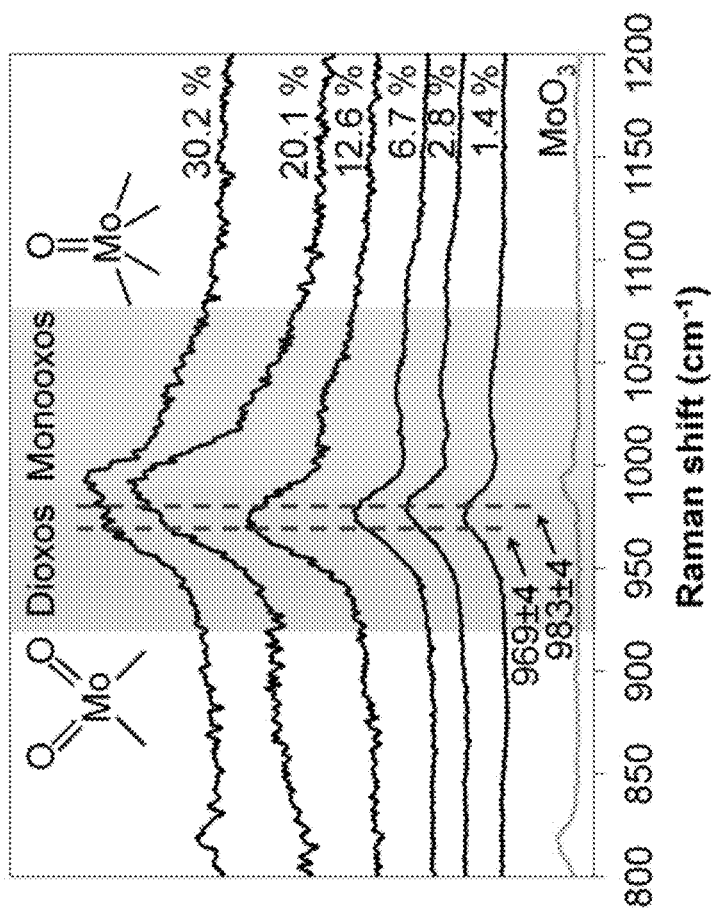
Figure 8D:
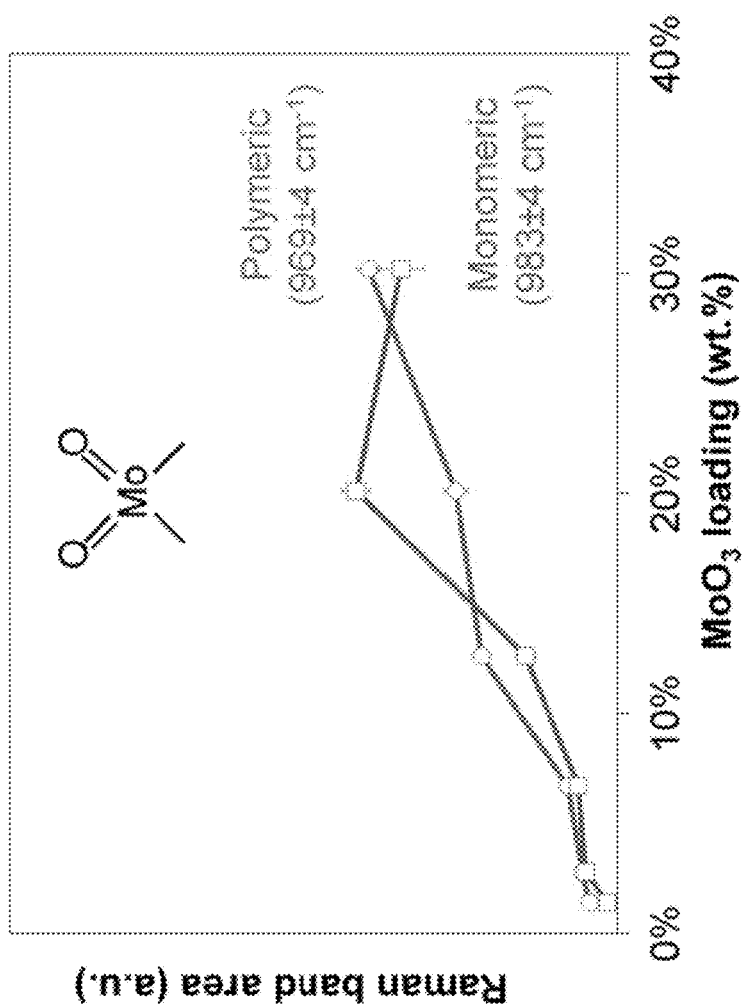

The data in FIG. 8D represent the average values from nine sets of fitting with band position shift of ±1 cm$^{-1}$, error bars represent standard deviations.

DETAILED DESCRIPTION

Methods of making activated supported heterogeneous metathesis catalysts and methods of using the activated supported heterogeneous metathesis catalysts are provided. Also provided are methods of regenerating deactivated supported heterogeneous metathesis catalysts. At least some embodiments of the disclosed activation and regeneration methods, which are both simple and cost-effective, are capable of providing activated and regenerated supported heterogeneous metathesis catalysts which characterized by high activity, high selectivity, high stability as well as ease of regeneration.

In one aspect, a method of making an activated supported heterogeneous metathesis catalyst is provided, comprising exposing a supported heterogeneous metathesis catalyst to an olefin compound for an activation time at an activation temperature. The exposure step serves to activate the supported heterogeneous metathesis catalyst for use in catalyzing a subsequent metathesis reaction (i.e., increase the activity and/or the selectivity of the activated supported heterogeneous metathesis catalyst as compared to the unactivated supported heterogeneous metathesis catalyst).

The supported heterogeneous metathesis catalysts comprise a support material and transition metal active groups impregnated in, or otherwise dispersed on, the support material. The supported heterogeneous metathesis catalyst is capable of catalyzing a metathesis reaction, e.g., an olefin metathesis reaction. Various supported heterogeneous metathesis catalysts may be used, including those made from various support materials and transition metal active groups. Exemplary support materials include $SiO_2$, $Al_2O_3$, $TiO_2$, $ZrO_2$, $B_2O_3$, $Ga_2O_3$, $GeO_2$, $SnO_2$ and mixtures thereof. The support material may be provided in various forms, e.g., particles, powders, fibers, membranes, and monoliths. Exemplary transition metal active groups include oxides of transition metals such as tungsten (W), e.g., $WO_3$, molybdenum (Mo), e.g., $MoO_3$, rhenium (Re), e.g., $Re_2O_7$, ruthenium (Ru), e.g., $RuO_2$, tantalum (Ta), e.g., $Ta_2O_5$, or niobium (Nb), e.g., $Nb_2O_5$.

Methods for forming the supported heterogeneous metathesis catalysts are known. Such methods may include exposing the support material to a solution comprising a precursor of the transition metal active group under conditions sufficient to impregnate the support material with the transition metal active group. Various precursors of the transition metal active group may be used. An exemplary precursor of $MoO_3$ is silicomolybdic acid, $H_4SiMo_{12}O_{40}$. An exemplary precursor of $WO_3$ is silicotungstic acid, $H_4SiW_{12}O_{40}$. Other methods for forming the supported heterogeneous metathesis catalysts include grafting, solution or vapor phase deposition, thermal spreading, sol-gel, spray-drying, flame synthesis, etc.

In the olefin activation process, various olefin compounds may be used and may depend upon the choice of supported heterogeneous metathesis catalyst. The olefin compounds may be cyclic or aliphatic, substituted or unsubstituted, linear or branched. The olefin compounds may comprise one or more carbon-carbon double bonds. The olefin compounds may have various numbers of carbon atoms, e.g., two, three, etc. Exemplary olefin compounds include ethylene, propylene, butenes, pentenes, and hexenes. Combinations of different olefin compounds may be used.

The olefin compound may be provided as a fluid (e.g., a gas or a liquid). The olefin compound may be provided pure or as part of a mixture with other components, e.g., a carrier. An exemplary carrier is an inert gas, e.g., $N_2$, He, Ne, or Ar. Various amounts of the olefin compound in the mixture may be used and may depend upon the choice of supported heterogeneous metathesis catalyst.

Various activation times and activation temperatures may be used and may depend upon the choice of supported heterogeneous metathesis catalyst. The activation temperature may be elevated such that it is greater than room temperature and may also be greater than the temperature (i.e., reaction temperature) at which the activated supported heterogeneous metathesis catalyst is used to catalyze a subsequent metathesis reaction. The activation temperature may be selected to be sufficiently high to convert metal-oxygen bonds to metal-carbon bonds in the activated supported heterogeneous metathesis catalyst but sufficiently low to limit the over-reduction of the metal oxide and to limit coking, in order to maximize the fraction of active transition metal sites. The present olefin activation processes may be distinguished from conventional activation processes employing hydrocarbons but which make use of significantly lower activation temperatures, typically activation temperatures which are substantially the same as the reaction temperatures of the metathesis reactions to be catalyzed by the activated supported heterogeneous metathesis catalysts.

For example, the activation temperature may be in the range of from about 200° C. to about 900° C. This includes embodiments wherein the activation temperature is in the range of from about 300° C. to about 800° C., from about 400° C. to about 700° C., from about 500° C. to about 600° C., from about 600° C. to about 900° C., from about 650° C. to about 800° C., etc. Regarding the activation time, as an example, the activation time may be in the range of from about 1 minute to about 1000 minutes. This includes embodiments in which the activation time is in the range of from about 1 minute to about 500 minutes, from about 1 minute to about 200 minutes, from about 1 minute to about 100 minutes, from about 10 minutes to about 100 minutes, etc.

The exposure step may involve exposure to more than one activation temperature during the activation time, e.g., a first activation temperature and a second activation temperature. For example, the exposure step may involve exposure at the first activation temperature, which is ramped to the second activation temperature at a temperature ramping rate. The exposure step may further involve exposure at the second activation temperature for a dwell time. The first and second activation temperatures, temperature ramping rates and dwell times may depend upon the choice of supported heterogeneous metathesis catalyst and may be selected as described above. For example, the first activation temperature may be in the range of from about 450° C. to about 550° C.; the second activation temperature may be in the range of from about 550° C. to about 800° C.; the temperature ramping rate may be in the range of from about 1° C./min to about 30° C./min; and the dwell time may be in the range of from about 10 minutes to about 100 minutes.

Prior to olefin activation, the supported heterogeneous metathesis catalysts may be subjected to one or more pre-activation steps, e.g., a calcination step (exposure to air for a selected time at a selected temperature) or a purging step (exposure to an inert gas for a selected time at a selected temperature). Subsequent to olefin activation, the activated supported heterogeneous metathesis catalysts may be subjected to one or more post-activation steps, e.g., a purging step or a cooling step. In the post-activation purging step, the selected temperature may be substantially the same as the activation temperature.

In some embodiments, a method of making an activated supported heterogeneous metathesis catalyst (e.g., a supported heterogeneous metathesis catalyst comprising transition metal oxide groups) comprises flowing a gas mixture comprising an olefin compound (e.g., propylene or ethylene) and a carrier (e.g., an inert gas) over the catalyst for an activation time at an activation temperature. The activation temperature may be greater than the temperature (i.e., reaction temperature) at which the activated supported heterogeneous metathesis catalyst is used to catalyze a subsequent metathesis reaction (e.g., an olefin metathesis reaction). The method may further comprise subsequently flowing an inert gas over the activated supported heterogeneous metathesis catalyst for a purging time at a purging temperature. The purging temperature may be substantially the same as the activation temperature.

In another aspect, a method of using the activated supported heterogeneous metathesis catalyst is provided, comprising exposing the activated supported heterogeneous metathesis catalysts to a reactant capable of undergoing a metathesis reaction for a reaction time at a reaction temperature to produce metathesis products. Exemplary reactants include unsaturated compounds, e.g., alkenes and alkynes. Exemplary metathesis reactions include olefin conversions such as on-purpose propylene production, short olefin to longer olefin conversions and a-olefin productions; ring-opening polymerizations; and alkyne conversions. If the selected reactant is itself an olefin, the reactant olefin may be the same (but need not be) as the olefin compound used in the olefin activation process described above. Reaction times and reaction temperatures and other reaction conditions may be selected depending upon the choice of supported heterogeneous metathesis catalyst and metathesis reaction. These reaction times, reaction temperatures and reaction conditions may be different from the activation times, activation temperatures and activation conditions described above. In this aspect, the exposure step reduces the activity and/or selectivity of the activated supported heterogeneous metathesis catalyst over time, thereby providing a deactivated supported heterogeneous metathesis catalyst. By deactivated, it is meant that the activity and/or the selectivity of the activated supported heterogeneous metathesis catalyst has been reduced as compared to the activated supported heterogeneous metathesis catalyst prior to deactivation. The activity and/or the selectivity of the deactivated supported heterogeneous metathesis catalyst may be have been reduced by a factor of at least 1.5, at least 2, at least 3, etc., as compared to an initial activity or initial selectivity of the activated supported heterogeneous metathesis catalyst as measured at an initial time point (e.g., substantially near t=0) during the reaction time. This includes embodiments in which the activity and/or selectivity of the activated supported heterogeneous metathesis catalyst has been reduced by a factor in the range of from about 1.5 to about 4.

In another aspect, a method of regenerating the deactivated supported heterogeneous metathesis catalyst is provided, comprising exposing the deactivated supported heterogeneous metathesis catalyst to a regenerating compound for a regeneration time at a regeneration temperature. The regenerating compound is capable of restoring the activity and/or selectivity of the deactivated supported heterogeneous metathesis catalyst. Thus, in this aspect, the exposure step provides a regenerated supported heterogeneous metathesis catalyst. By regenerated, it is meant that the activity and/or the selectivity of the deactivated supported heterogeneous metathesis catalyst has been increased as compared to the deactivated supported heterogeneous metathesis catalyst prior to regeneration. The activity and/or the selectivity of the regenerated supported heterogeneous metathesis catalyst may have been increased by at least 50%, to at least 75%, to at least 95%, etc., as compared to the initial activity or initial selectivity of the activated supported heterogeneous metathesis catalyst (which was subsequently deactivated). In some embodiments, the activity and/or the selectivity of the regenerated supported heterogeneous metathesis catalyst is substantially the same as the activated supported heterogeneous metathesis catalyst prior to deactivation. In some embodiments, the activity and/or the selectivity of the regenerated supported heterogeneous metathesis catalyst is greater than the activated supported heterogeneous metathesis catalyst (which was subsequently deactivated). (See, e.g., FIG. 1D.) In some embodiments, the activity and/or the selectivity of the regenerated supported heterogeneous metathesis catalyst is within about ±10% or ±5% of the activity and/or the selectivity of the activated supported heterogeneous metathesis catalyst prior to deactivation. The regeneration step may be repeated multiple times, e.g., two times, three times, etc.

In one embodiment, the regeneration method comprises repeating the olefin activation process described above, but using the deactivated supported heterogeneous metathesis catalyst (instead of the supported heterogeneous metathesis catalyst). Thus, the regenerating compound is the olefin compound used in the olefin activation process described above, the regeneration time is the activation time described above and the regeneration temperature is the activation temperature described above.

In another embodiment, the regeneration method comprises exposing the deactivated supported heterogeneous metathesis catalyst to an inert gas (or inert gas mixture) for a regeneration time at a regeneration temperature. In some embodiments, the regeneration method does not comprise the use of air or oxygen. Various regeneration times and regeneration temperatures may be used and may depend upon the choice of supported heterogeneous metathesis catalyst, the choice of metathesis reaction and the extent of deactivation. The regeneration temperature may be selected to maximize the activity and/or the selectivity of the regenerated supported heterogeneous metathesis catalyst. An exemplary regeneration temperature is at least 200° C., at least 250° C., at least 300° C., at least 400° C., at least 500° C., at least 600° C., at least 700° C., etc. This includes regeneration temperatures in the range of from about 200° C. to about 800° C. or in the range of from about 300° C. to about 800° C. An exemplary regeneration time is in the range of from about 1 minute to about 1000 minutes. This includes embodiments in which the regeneration time is in the range of from about 1 minute to about 500 minutes, from about 1 minute to about 200 minutes, from about 1 minute to about 100 minutes, from about 10 minutes to about 100 minutes, etc.

The regeneration methods may be used to regenerate supported heterogeneous metathesis catalysts which may have been used to catalyze a metathesis reaction (thereby becoming deactivated) but which may not have been activated prior to catalyzing the metathesis reaction. Alternatively, the supported heterogeneous metathesis catalyst may have been activated prior to catalyzing the metathesis reaction, but may have been activated by other activation methods, e.g., via a conventional activation procedure such as calcination in air. Finally, the regeneration methods may be used to regenerate supported heterogeneous metathesis catalysts which have been deactivated by other methods, e.g., via $O_2$ or $H_2O$ poisoning.

Also provided are the activated supported heterogeneous metathesis catalysts and the regenerated supported heterogeneous metathesis catalysts. As described above, the catalysts may be characterized by the activity and the selectivity. The activity may be quantified by various ways, including percentage of metathesis reactant converted, weight-based activity, etc. The activity may be quantified as a turnover frequency (TOF), as measured at the initial time point (e.g., substantially near t=0) during the reaction time of the catalyst and the reaction temperature used. The activity may also be quantified as an accumulated turnover number (TON), as measured over the reaction time of the catalyst and the reaction temperature used. The selectivity may be quantified as a percentage of a particular type of metathesis product. The catalysts may be characterized by a TOF of at least $10^2$/h, at least $10^3$/h, at least $10^4$/h, at least $10^5$/h, etc. This includes TOF in the range of from about 10/h to about $10^5$/h, from about $10^2$/h to about $10^4$/h, etc. The catalysts may be characterized by a TON of at least $10^4$, at least $10^5$, at least $10^6$, etc. The catalysts may be characterized by a selectivity of at least 95%, at least 98%, at least 99.5%, etc.

The activated and regenerated supported heterogeneous metathesis catalysts may be characterized by the fraction of active metal sites. The fraction of active metal sites may be at least 3%, at least 4%, at least 5%, at least 50%, or even 100%. This includes embodiments in which the fraction of active metal sites is in the range of from about 1% to about 11%, from about 3% to about 5%, etc. These values may refer to a loading of transition metal active groups (e.g., transition metal oxide active groups) corresponding to about a monolayer coverage of transition metal active groups on the support material.

Unless otherwise specified, any numerical values recited for the chemical or physical properties of the activated, deactivated, or regenerated supported heterogeneous metathesis catalysts refer to values measured according to the techniques described in the Example. For example, TOF, TON and selectivity values were measured using an atmospheric pressure fixed bed flow reactor system configured with gas chromatography with reaction conditions (e.g., reaction temperature and metathesis reactant flow) selected to maximize activity/selectivity. Active metal sites were measured using isotope tracing.

EXAMPLE

Summary

This Example shows that after a very simple pretreatment in olefin-containing atmosphere at elevated temperatures, the low temperature olefin metathesis activities of the wet impregnated $MoO_3/SiO_2$ and $WO_3/SiO_2$ were increased by a factor of 100 (TOF dramatically increased from less than 3/h to ~$10^3$/h), which are comparable with supported organometallic catalysts. (See, N. Popoff, E. Mazoyer, J. Pelletier, R. M. Gauvin, M. Taoufik, *Chem. Soc. Rev.* 42, 9035 (2013); Y. Iwasawa, H. Ichinose, S. Ogasawara, M. Soma, *J. Chem. Soc., Faraday Trans.* 77, 1763 (1981); M. Chabanas, A. Baudouin, C. Coperet, J. M. Basset, *J. Am. Chem. Soc.* 123, 2062 (2001); A. Salameh et al., *J. Catal.* 253, 180 (2008); E. Mazoyer et al., *J. Catal.* 301, 1 (2013) and N. Popoff et al., *Chemcatchem* 5, 1971 (2013).) The selectivity of metathesis products is greater than 99.5%, with less than 0.5% isomerization products. Turnover number up to $10^4$ can be achieved. More importantly, these catalysts can be regenerated by simply inert gas purging at elevated temperatures. Furthermore, the ability to manipulate the concentration of active sites in combination with spectroscopy and electron microscopy measurements was used to unambiguously identify the monomeric nature of the active sites for $MoO_3/SiO_2$ catalysts. This provides valuable guidance for rational design of high-performance oxide-based olefin metathesis catalysts.

Materials and Methods

Synthesis of $SiO_2$ Support 12.5 g of poly(ethylene oxide) (Mw=$10^5$, Sigma Aldrich) was dissolved in 125 g of 1M HNO3 in a VWR KIMAX Media/Storage Bottle (500 ml size) at room temperature. 81.25g of tetraethyl orthosilicate (98%, Sigma Aldrich) was added to the solution, sealed, shook vigorously until the solution became homogeneous. The solution was stirred on a stir plate at room temperature for 30 min. The bottle was then transferred to an oven preheated to 40° C. and stood for 2.5 days. The resulted monolithic white gel was cut into small pieces (<10 mm) and immersed in 300 ml of DI $H_2O$ in order to soak out the acid remained in the gel. The solvent was changed every 2 hours. The $4^{th}$ solvent was 0.045M $NH_3H_2O/H_2O$. The bottle was sealed and kept in a 40° C. oven for 24 h. The gel particles were then rinsed with DI $H_2O$ and dried at 40° C. for 24 h, and then at 100° C. for 12 h. The dried gel particles were calcined in air with a temperature ramping rate of 1.5° C./min up to 600° C., dwelt at 600° C. for 12 h. The overall pore volume of the $SiO_2$ was ca. 5 $cm^3$/g, including macropores, mesopores, and micropores.

Synthesis of $MoO_3/SiO_2$ and $WO_3/SiO_2$

Desired amount of $H_4SiMo_{12}O_{40}$ or $H_4SiW_{12}O_{40}$ was dissolved and diluted to 30 ml using DI $H_2O$ and then added to 6 g of $SiO_2$ (crushed into 20-40 mesh size particles) in a plastic tube and shook for 5 min. The solution was fully absorbed by the $SiO_2$ particles quickly. The impregnated $SiO_2$ particles were transferred to a petri dish and dried at 40° C. for 24 h, and then at 100° C. for 12 h. The dried particles were calcined in air with a temperature ramping rate of 1.5° C./min up to 600° C., dwelt at 600° C. for 10 h.

In control experiments, $(NH_4)_2MoO_4$ was used as an alternative Mo precursor for wet-impregnation. A commercial $SiO_2$ (Grace Davison, BET specific surface area of 360 $m^2$/g, pore volume of 1.4 $cm^3$/g) was used as an alternative $SiO_2$ support for wet-impregnation. The impregnation, drying, and calcination procedures are the same with that described above, except that 1.4 ml of aqueous Mo precursor solution per gram of $SiO_2$ was used for the commercial $SiO_2$.

Propylene Metathesis, Mechanistic Studies, and Active Site Counting

Figure 4:
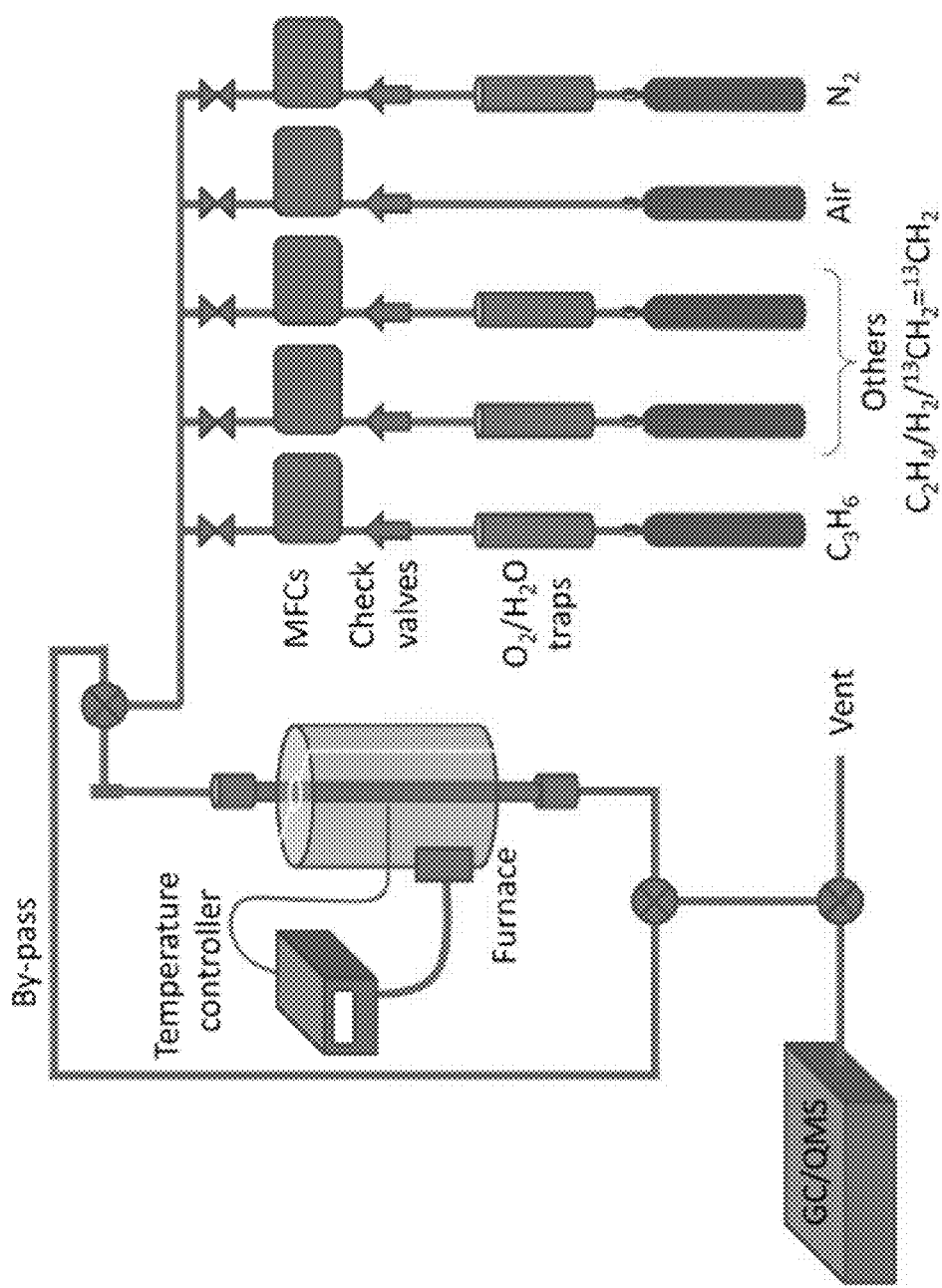
FIG. 4 shows a schematic illustration of the atmospheric pressure fixed bed flow reactor system which was used for the metathesis reactions described in the Example.

The propylene metathesis reactions were conducted in an atmospheric pressure fixed bed flow reactor system with 3/8" stainless steel reactor, as illustrated in FIG. 4. All C2-C4 olefins were provided by Matheson Tri-Gas in UHP grade. Research purity $N_2$ was provided by Airgas. $C_3H_6$ and $N_2$ were further purified over oxygen/moisture traps (VICI). The gas flow rates were controlled by mass flow controllers (MKS Instruments). The products were analyzed by an on-line Agilent 3000A microGC equipped with MS-5A ($O_2$, $N_2$, $CH_4$, CO), Plot U ($CO_2$, $C_2H_4$, $C_2H_6$) and Alumina (C2-C5 alkanes and olefins) columns. Each column was connected to a separate thermal conductivity detector. $N_2$ was used as internal standard for GC quantification.

A Quadrupole mass spectrometer (SRS RGA200) was used for on-line MS studies, including activation and regeneration mechanistic studies and active site counting.

A typical procedure for the active site counting studies using $C_2H_4$ was as follows. 200 mg of $MoO_3/SiO_2$ was calcined in air (50 sccm) at 550° C. for 30 min, then purged with $N_2$ (100 sccm) at 550° C. for 30 min; activated in $C_3H_6:N_2$=4 sccm:96 sccm at 550° C. for 30 min, then purged with $N_2$ (100 sccm) at 550° C. for 10 min, cooled down to 20° C. under $N_2$ (100 sccm); switched to $C_3H_6:N_2$=40 sccm:5 sccm for 10 min, then purged with $N_2$ (100 sccm) for 20 min; switched to $^{13}C_2H_4:N_2$=1 sccm:44 sccm for 10 min, then purged with $N_2$ (100 sccm) for 20 min.

UV Resonance Raman and Visible Raman Studies

In situ UV (244 nm) resonance Raman and visible (488 nm) studies $MoO_3/SiO_2$ and $WO_3/SiO_2$ catalysts were conducted on a home-built Raman instrument. The 244 nm excitation was produced by a Lexel 95 SHG (second harmonic generation) laser equipped with an intracavity non-linear crystal, BBO ($BaB_2O_4$), which doubles visible radiation frequency into the mid-ultraviolet region. Raman spectra were collected at room temperature under a He atmosphere using a fluidized bed reactor. The samples were dehydrated at 550° C. for 30 min in 20/80 (v/v) $O_2$/He and purged with He for 30 min before cooled down to room temperature. The power of UV laser was 4.5 mW, and the total data collection time was 40 min. The power of visible laser was 40 mW, and the total data collection time varied with sample. The Raman shift was calibrated by measuring cyclohexane as standard. The UV Raman spectra are normalized by the region of Si—O vibrations (400-700 $cm^{-1}$).

Characterizations

Nitrogen sorption isotherms were measured at 77 K on a Micromeritics ASAP 2010 (USA). Before measurements, the samples were degassed under vacuum at 250° C. for at least six hours. The Brunauer-Emmett-Teller (BET) method was utilized to calculate the specific surface areas. By using the Barrett-Joyner-Halenda (BJH) model, the pore volumes and pore size distributions were derived from the desorption branches of the isotherms.

Powder X-ray diffraction (XRD) patterns were collected on a Rigaku Ultima diffractometer with Cu Kα radiation.

Scanning electron microscopy (SEM) observations and energy dispersive X-ray spectroscopy analyses were conducted on Hitachi SU8030.

Transmission electron microscopy (TEM) and selected area electron diffraction (SAED) analyses were conducted on a JEOL JEM-2100 FasTEM operating at 200 kV. High spatial resolution HAADF imaging with an inner diameter of 68 mrad and outer 230 mrad was performed on a JEOL JEM-ARM200CF electron microscope, with a probe side Cs-corrector yielding a probe size of approximately 0.078 nm, operating at 200 kV. Under daily operating conditions, the third order aberrations can remain stable for days while the second order aberrations were monitored and corrected as needed during the experiments. Dry powder specimens on a Cu grid with a carbon film support were used for these electron microscopy characterizations to minimize contamination.

UV-Vis diffuse reflectance spectra were recorded at room temperature on a Perkin Elmer LAMBDA 1050 spectrophotometer equipped with a diffuse-reflectance attachment. Before taking UV-Vis DRS spectra, the samples were dehydrated at 450° C. for 10 h and then transferred into a dessicator. These powder samples were then loaded in a glovebox, into a sample holder sealed with a quartz window, and were then rapidly mounted in the spectrometer. The sample thickness was greater than 2 mm. The UV-Vis DRS spectra were transformed into Kubelka-Munk units, $F(R_\infty) = (1-R_\infty)^2/2R_\infty$, where $R_\infty$ is the experimentally measured reflectivity coefficient of the samples using $BaSO_4$ as a reference.

In-situ FTIR spectra were acquired using a Nicolet 6700 infrared spectrometer equipped with a liquid nitrogen cooled MCT (mercury-cadmium-telluride) detector which allowed for measurement of IR spectra from 1000 to 4000 $cm^{-1}$. The samples were mounted in an IR cell customized for transmission mode studies of powder samples that are supported on a tungsten grid (~2 $cm^2$) that can be heated. The samples were heated in the cell at 550° C. for 30 min before being cooled to room temperature for spectrum acquisitions. The dehydration process was performed under vacuum (~$10^{-5}$ torr) in order to avoid failure of the tungsten grid. All the spectra were recorded using 128 scans and a resolution of 4 $cm^{-1}$. The infrared spectra are normalized by the amount of $SiO_2$ contained in the samples for the comparison of the silanol OH stretching band.

Figure 1A:
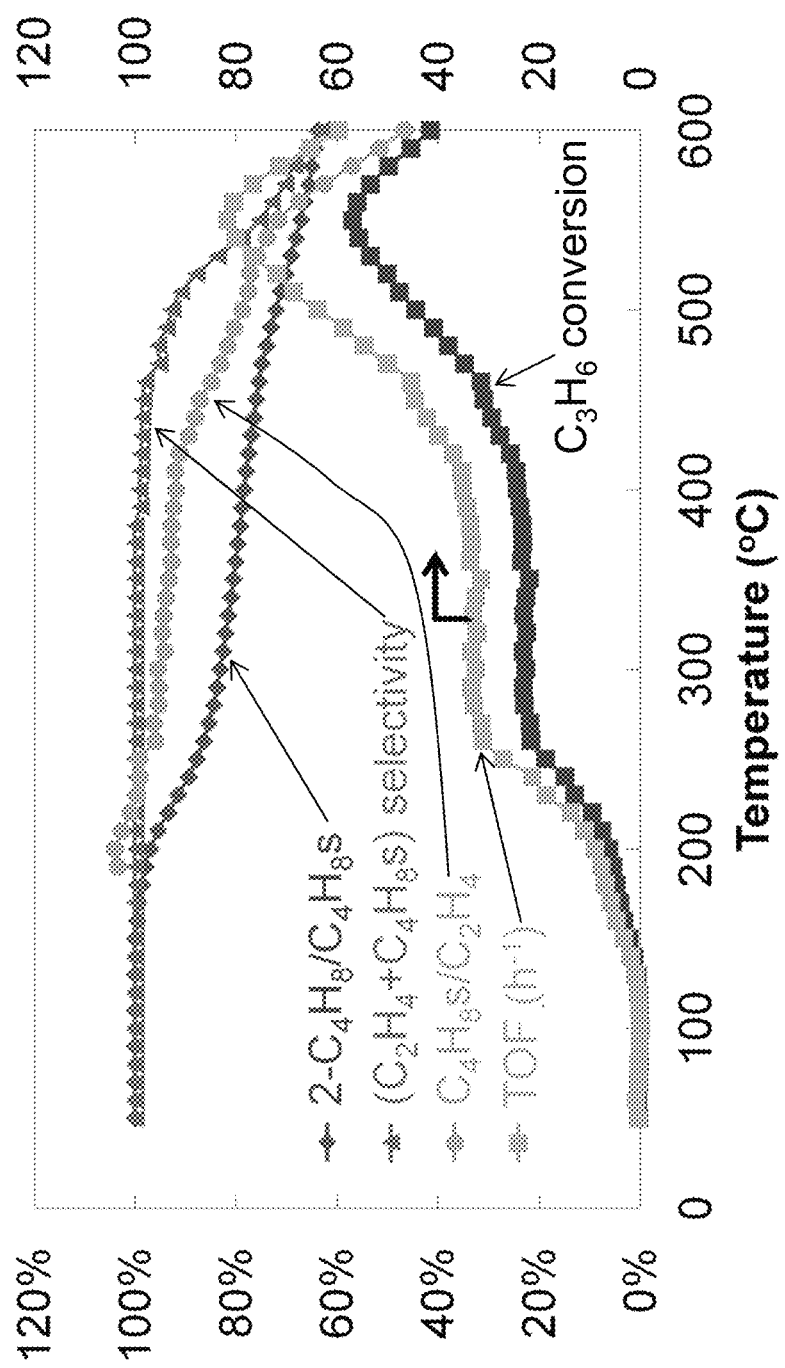
FIGS. 1A-1F show TPRx of propylene metathesis over $MoO_3/SiO_2$ (FIG. 1A) and $WO_3/SiO_2$ (FIG. 1B); propylene metathesis over propylene activated $MoO_3/SiO_2$ (FIGS. 1C and 1E) and $WO_3/SiO_2$ (FIGS. 1D and 1F). Reaction conditions of FIGS. 1A and 1B: 550° C., calcined in air (50 sccm) for 60 min, purged with $N_2$ (100 sccm) for 60 min, cooled down to 50° C. in $N_2$ (100 sccm), switched to $C_3H_6$:$N_2$=5 sccm:5 sccm; reaction temperature was increased from 50-600° C. (Mo) or 50-700° C. (W), with a ramp rate of 1° C./min. Reaction conditions of FIGS. 1C to 1F: 550° C., calcined in air (50 sccm) for 30 min, purged with $N_2$ (100 sccm) for 30 min; $MoO_3/SiO_2$ was activated in $C_3H_6$:$N_2$=4 sccm:96 sccm at 550° C. for 30 min, then purged with $N_2$ (100 sccm) at 550° C. for 10 min, cooled down to room temperature in $N_2$ (100 sccm), switched to $C_3H_6$:$N_2$=40 sccm:5 sccm; $WO_3/SiO_2$ was activated in $C_3H_6$:$N_2$=4 sccm:96 sccm, temperature was increased from 550-700° C. with a ramp rate of 10° C./min, dwelt at 700° C. for 30 min, then purged with $N_2$ (100 sccm) at 700° C. for 10 min, cooled down to 200° C. in $N_2$ (100 sccm), switched to $C_3H_6$:$N_2$=80 sccm: 10 sccm. The $1^{st}$ regeneration in FIGS. 1C and 1D was conducted via calcination in air following by re-activation in propylene as described above. The $2^{nd}$ and $3^{rd}$ regenerations were conducted via $N_2$ purging at 550° C. (Mo) or 700° C. (W) for 10 min.
Figure 1B:
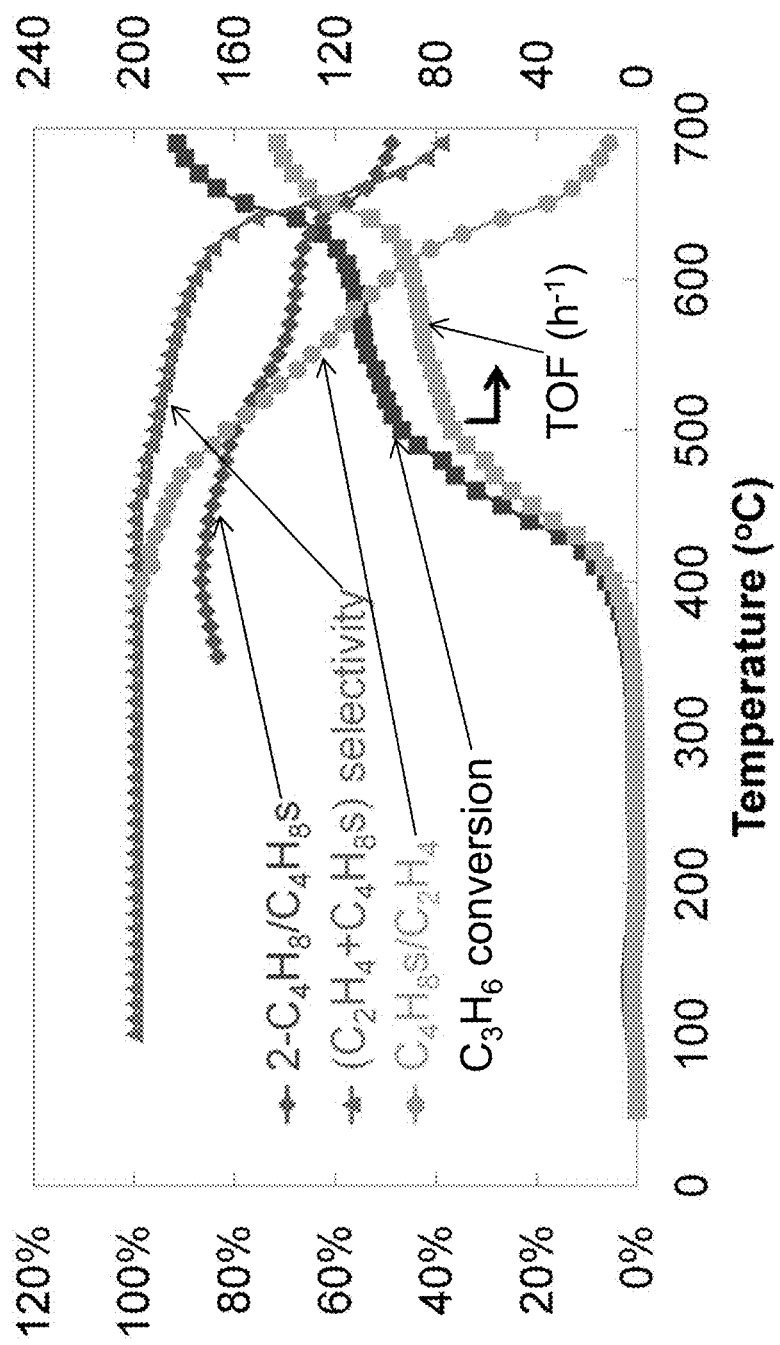

Results and Discussion $MoO_3/SiO_2$ and $WO_3/SiO_2$ with loading of 7 wt. % and 10 wt. % were prepared via wet impregnation of $H_4SiMo_{12}O_{40}$ and $H_4SiW_{12}O_{40}$ into a high surface area $SiO_2$ support, following by drying and calcination. Propylene metathesis reaction was tested over these catalysts. FIG. 1A shows the temperature programmed reaction spectra (TPRx) of the $MoO_3/SiO_2$ after a conventional activation process which includes high temperature calcination and inert gas purging. The propylene conversion is less than 1% at a reaction temperature below 130° C. It then ramps up with reaction temperature and reaches a plateau between 260° C. and 400° C., then it ramps up again and reaches a maximum at 550° C. and then drops. The propylene conversion curve implies a competition between activation and deactivation process during the temperature-programmed reaction.

Figure 1C:
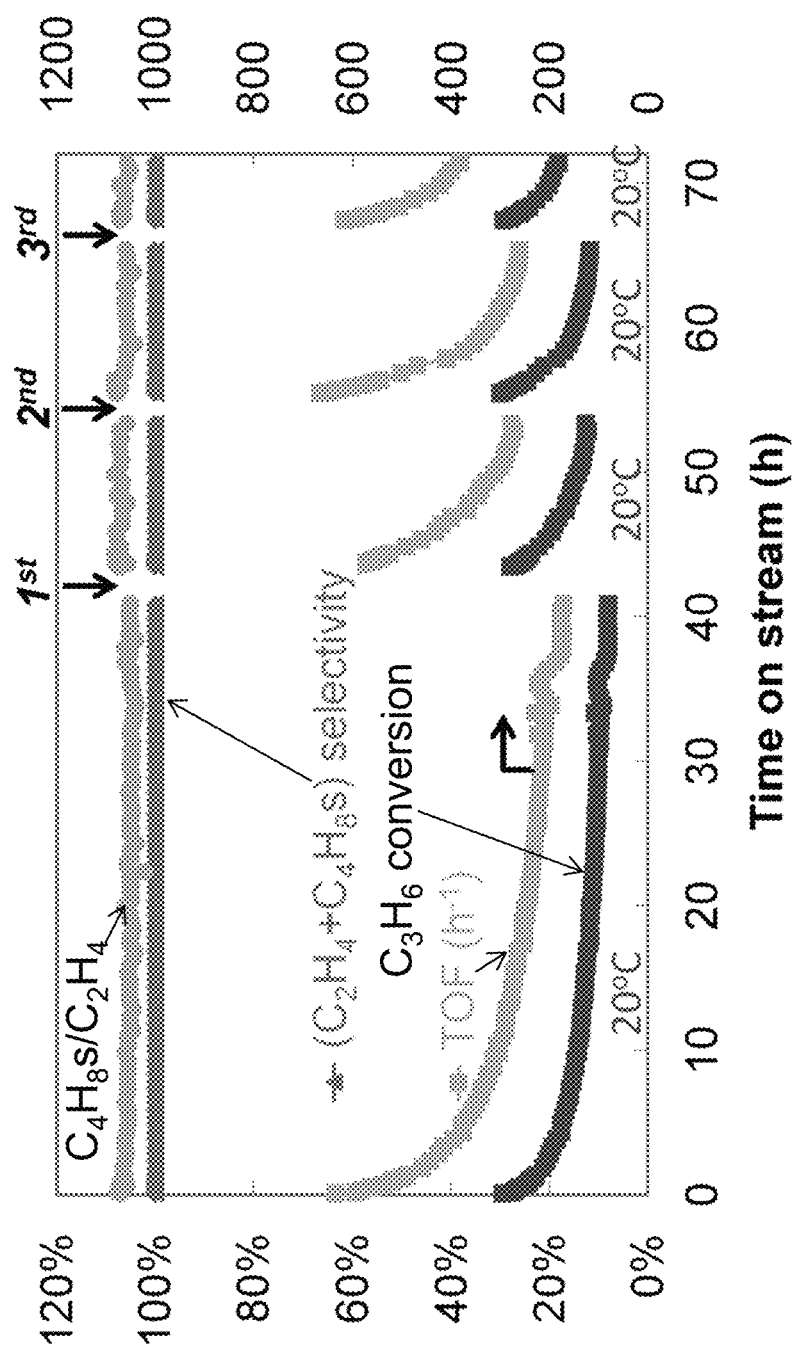
Figure 1D:
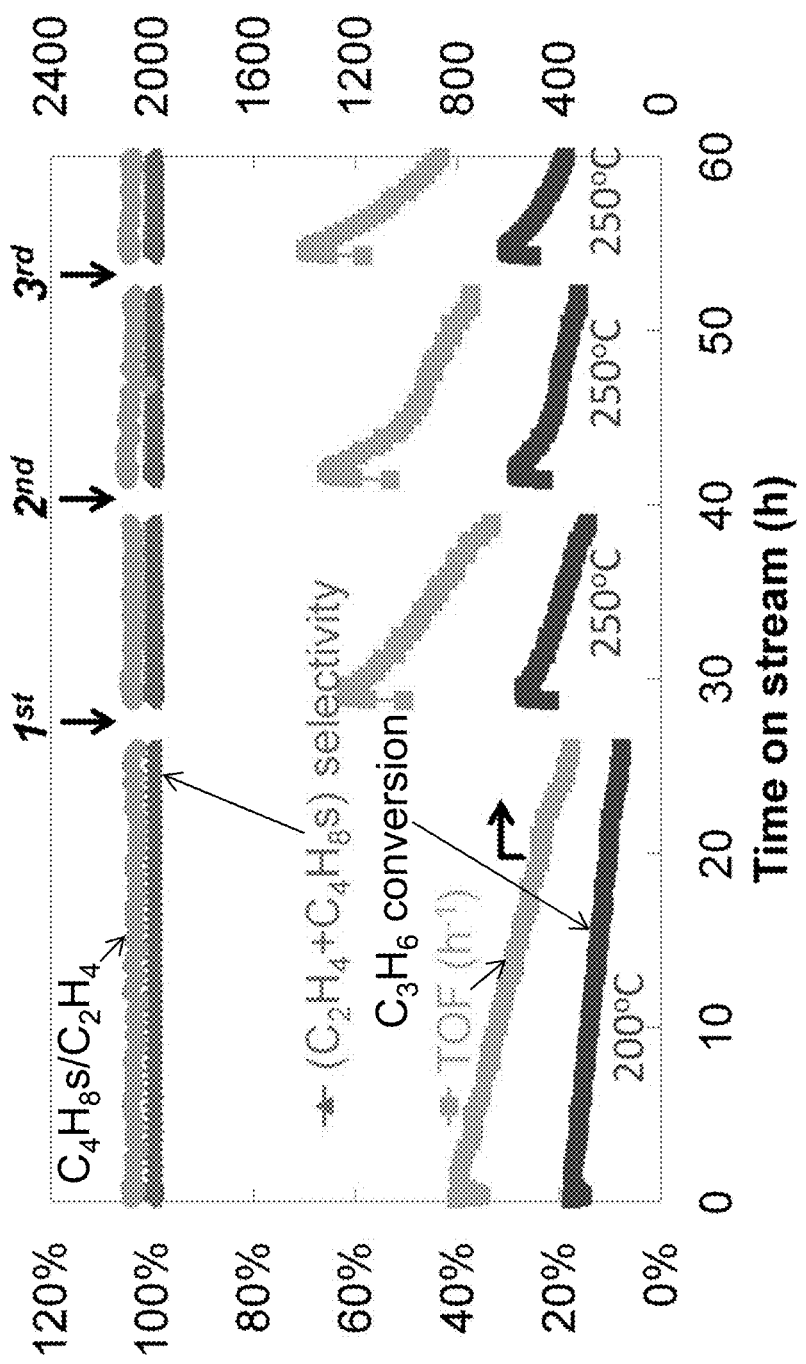
Figure 1E:
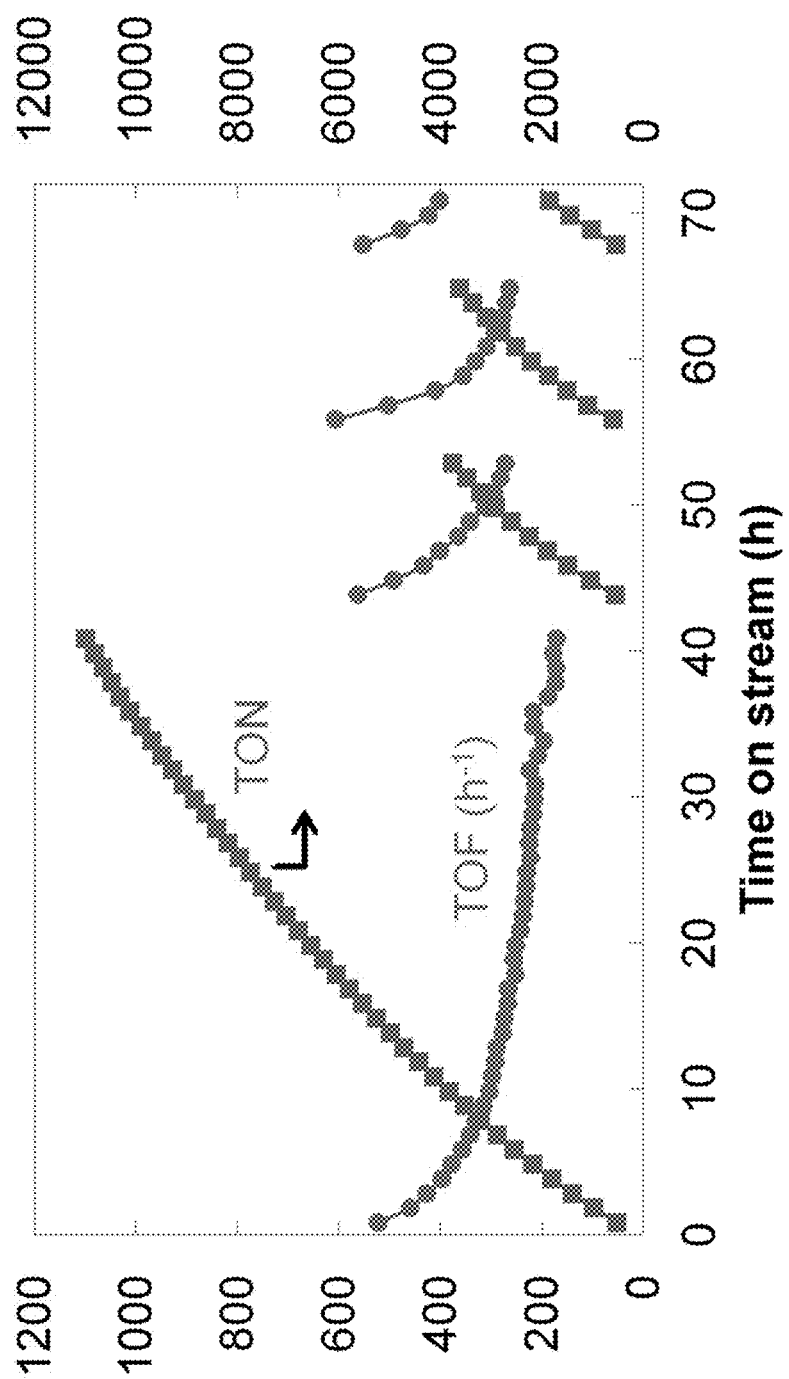
Figure 1F:
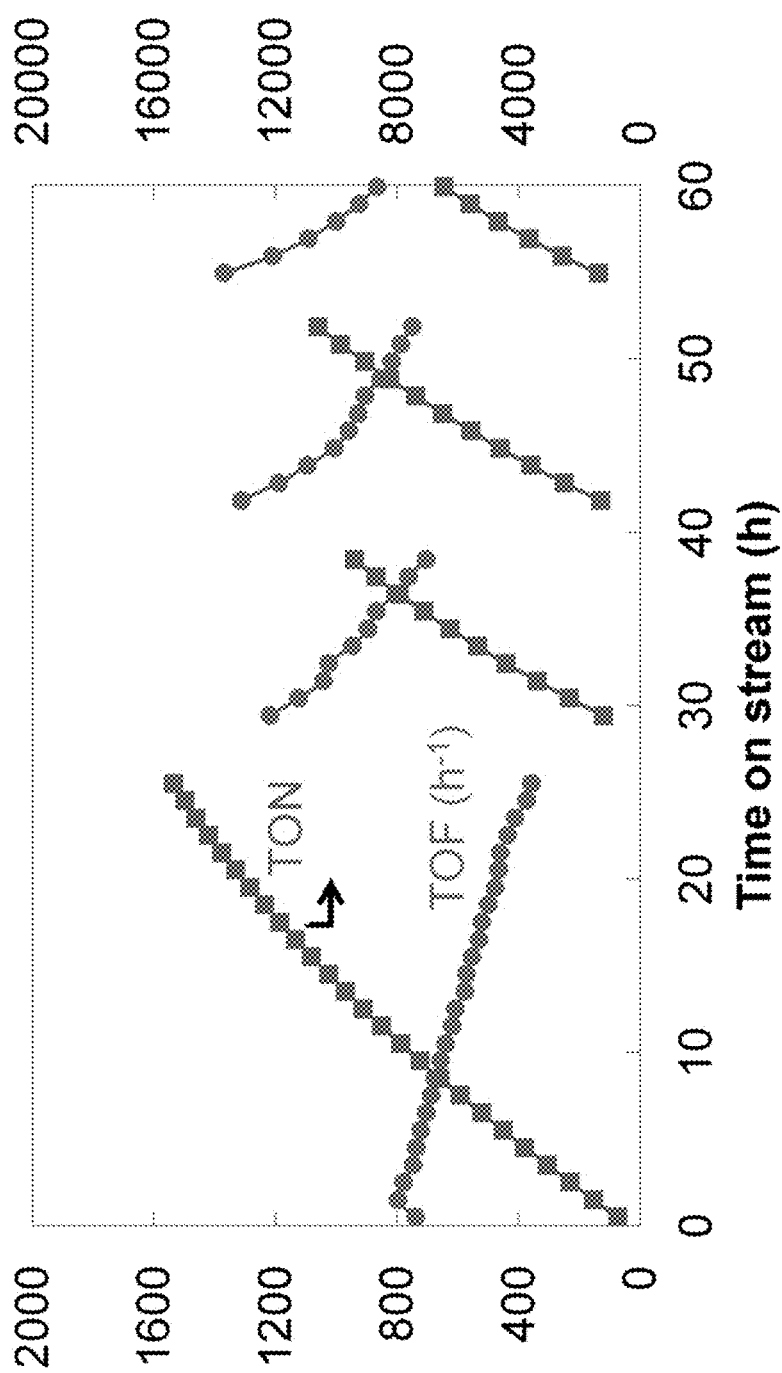

The activation procedure was studied by varying the propylene concentration, activation temperature, and activation time. In most cases, the $MoO_3/SiO_2$ samples pretreated in propylene at high temperature show one to two orders of magnitudes higher activity in propylene metathesis at room temperature compared to that pretreated by calcination and inert gas purging. The best result was obtained via 4/96 (v/v) propylene/$N_2$ pretreatment at 550° C. for 30 min with an additional inert gas purging for 10 min at the same temperature. FIG. 1C shows the room temperature propylene metathesis performance of $MoO_3/SiO_2$ after such an optimized activation procedure. The initial turnover frequency (TOF calculation based on the total amount of metal) of propylene metathesis is over 600/h, which is more than two orders of magnitudes higher than that pretreated by calcination and inert gas purging. This is equal to a weight-based activity of 300 mmol/(gcat·h). The products are solely ethylene and 2-butenes, with molar ratio close to 1. No isomerization product was observed. The metathesis activity gradually declines with time-on-stream. The accumulative turnover number (TON) reaches $1.1 \times 10^4$ in 40 hours (FIG. 1E). The catalytic activity can be fully restored via calcination followed by re-activation in propylene. Unexpectedly, simple inert gas purging at 550° C. also fully restores the catalytic activity. Regenerated catalysts via both pathways behave the same with freshly activated catalyst. This is the first time that inert gas purging has been shown to completely regenerate an olefin metathesis catalyst. Taking into account that none of the organometallic olefin metathesis catalysts can be easily regenerated, this discovery of a regeneration pathway is remarkable. This type of nonoxidative regeneration could be advantageous for industrial applications because of its simplicity and low heat generation.

Compared to supported molybdenum oxides, a supported tungsten oxide usually requires higher reaction temperature to give an appreciable olefin metathesis activity because of its comparatively poor reducibility. (See, J. C. Mol, P. W. N. M. van Leeuwen, in *Handbook of Heterogeneous Catalysis*. (2008), vol. 14, pp. 3240-3256 and N. Popoff, E. Mazoyer, J. Pelletier, R. M. Gauvin, M. Taoufik, *Chem. Soc. Rev.* 42, 9035 (2013).) As shown in FIG. 1B the TPRx behavior of $WO_3/SiO_2$ is similar to that of $MoO_3/SiO_2$, except that the propylene conversion ramps up at higher temperature. After a 30 min pretreatment in 4/96 (v/v) propylene/$N_2$ at 700° C. with an additional 10 min inert gas purging at the same temperature, the low temperature propylene metathesis activity of $WO_3/SiO_2$ greatly increases. The initial TOF of propylene metathesis at 200° C. is 800/h, which is three orders of magnitudes higher than that pretreated by calcination and inert gas purging. This is equal to a weight-based activity of 360 mmol/(gcat·h). After a calcination and re-activation process, the propylene metathesis reaction at 250° C. was tested, and an initial TOF of 1200/h was achieved. This is equal to a weight-based activity of 540 mmol/(gcat·h). Similar to the regeneration of $MoO_3/SiO_2$, an inert gas purging at 700° C. also fully restores the catalytic activity. The accumulative TON reaches $1.5 \times 10^4$ in 25 hours at the reaction temperature of 200° C., and it reaches $10^4$ in 10 hours at 250° C. The selectivity of 2-butenes in total butene products is greater than 99.5%, with less than 0.5% of isomerization product formation.

Compared to the most active, reported $MoO_3$-$Al_2O_3$-$SiO_2$ catalysts made by flame synthesis (D. P. Debecker et al., *J. Catal.* 277, 154 (2011)) and aerosol synthesis (D. P. Debecker et al., *Angew. Chem. Int. Ed.* 51, 2129 (2012)), the present activated $MoO_3/SiO_2$ and $WO_3/SiO_2$ catalysts catalysts have more than one order of magnitude higher activity. The catalytic performance is comparable to high-performance, supported organometallic catalysts (N. Popoff, E. Mazoyer, J. Pelletier, R. M. Gauvin, M. Taoufik, *Chem. Soc. Rev.* 42, 9035 (2013); Y. Iwasawa, H. Ichinose, S. Ogasawara, M. Soma, *J. Chem. Soc., Faraday Trans.* 77, 1763 (1981); M. Chabanas, A. Baudouin, C. Coperet, J. M. Basset, *J. Am. Chem. Soc.* 123, 2062 (2001); A. Salameh et al., *J. Catal.* 253, 180 (2008); E. Mazoyer et al., *J. Catal.* 301, 1 (2013).

Since the widely accepted Hérisson-Chauvin olefin metathesis mechanism is based on metallocarbene and metallacyclobutane intermediates, converting the metal oxo (M=O) into metallocarbene or metallacyclobutane is the key to the activation of supported oxide based olefin metathesis catalysts. In order to understand the activation procedure of $MoO_3/SiO_2$ and $WO_3/SiO_2$, online gas chromatography (GC) and mass spectrometer (MS) was used to monitor the gaseous products generated during the activation process, UV-Raman spectrometer to study the structure evolution of catalysts.

Except these expected propylene metathesis products, ethylene and butenes with molar ratio of 1, other products were generated in the activation process including $CH_4$, ethylene (excess amount of non-metathesis ethylene), CO, $CO_2$, $H_2$, $H_2O$ and benzene, as shown in FIGS. 2A-2G. On-line GC and MS analysis of the gaseous products generated during the temperature-programmed reaction process over $MoO_3/SiO_2$ was performed. The reaction conditions were 200 mg of 7 wt. % $MoO_3/SiO_2$, calcined in air (50 sccm) at 550° C. for 60 min, purged with $N_2$ (100 sccm) at 550° C. for 60 min; cooled down to 50° C. under $N_2$ (100 sccm); switched to $C_3H_6$:$N_2$=4 sccm:96 sccm, 50-600° C., ramp rate of 1° C./min. On-line GC and MS analysis of the gaseous products generated during the temperature-programmed reaction process over $WO_3$/$SiO_2$ was also performed. The reaction conditions were 200 mg of 10 wt. % $WO_3$/$SiO_2$, calcined in air (50 sccm) at 550° C. for 60 min, purged with $N_2$ (100 sccm) at 550° C. for 60 min; cooled down to 50° C. under $N_2$ (100 sccm); switched to $C_3H_6$:$N_2$=4 sccm:96 sccm, 50-750° C., ramp rate of 1° C./min. The results showed that $CH_4$, CO, $H_2$ and benzene start forming at about 500° C. on $MoO_3$/$SiO_2$, and at about 600° C. on $WO_3$/$SiO_2$. GC analyses of the gaseous products generated during the temperature-programmed propylene metathesis over bare $SiO_2$ (sol-gel) were also performed. The reaction conditions were 200 mg of $SiO_2$, calcined in air (50 sccm) at 550° C. for 60 min, purged with $N_2$ (100 sccm) at 550° C. for 60 min; cooled down to 50° C. under $N_2$ (100 sccm); switched to $C_3H_6$:$N_2$=4 sccm:96 sccm; temperature was increased from 50-750° C. with a ramp rate of 1° C./min. The results showed that bare $SiO_2$ support gave negligible propylene conversion up to 700° C.

Figure 2A:
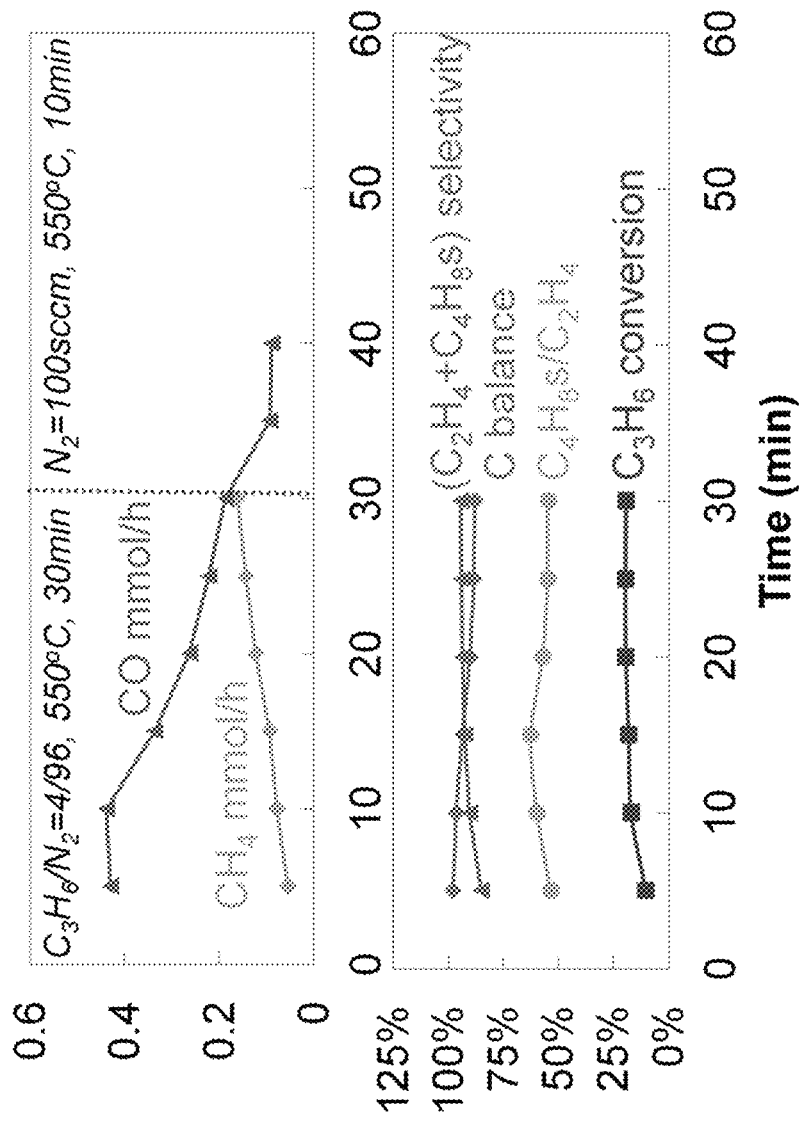
FIGS. 2A-2G relate to the activation and regeneration mechanisms.
Figure 2B:
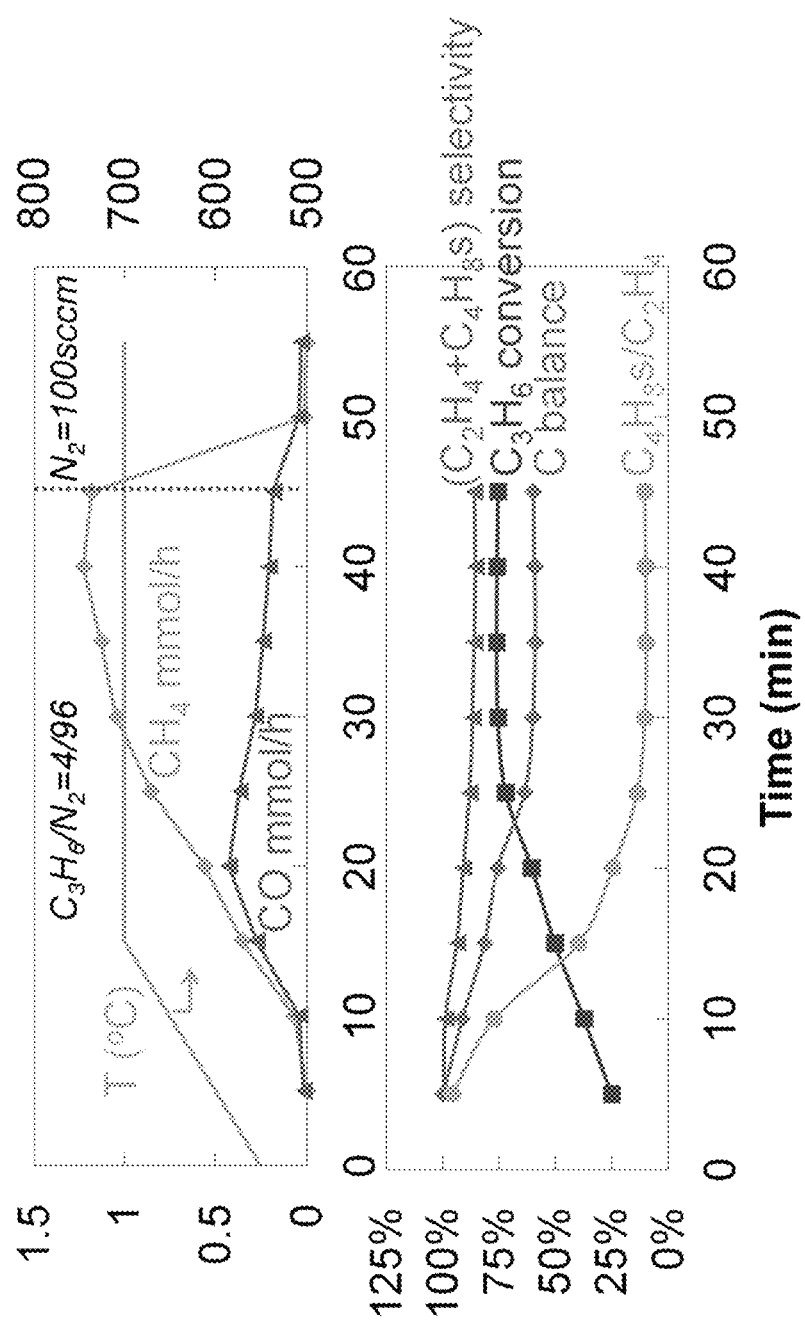
Figure 2C:
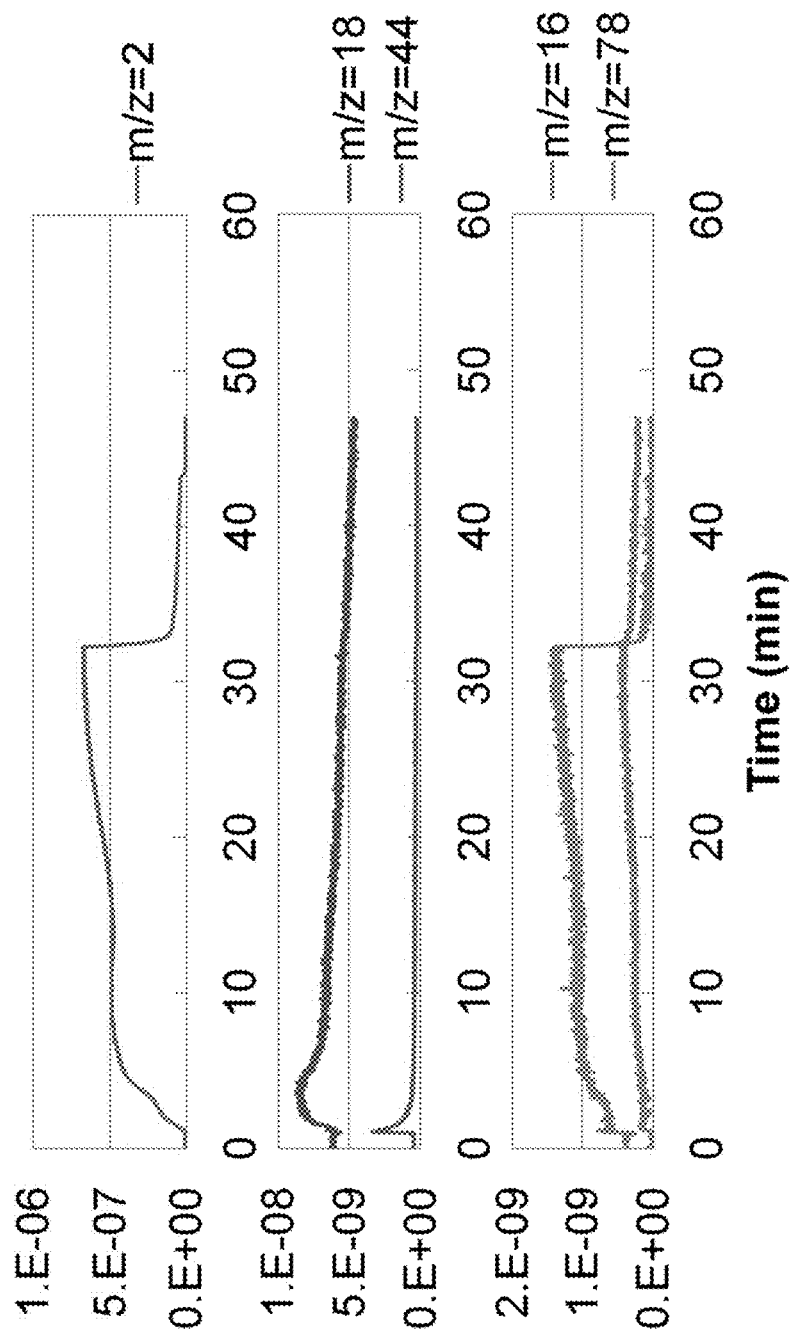
Figure 2D:
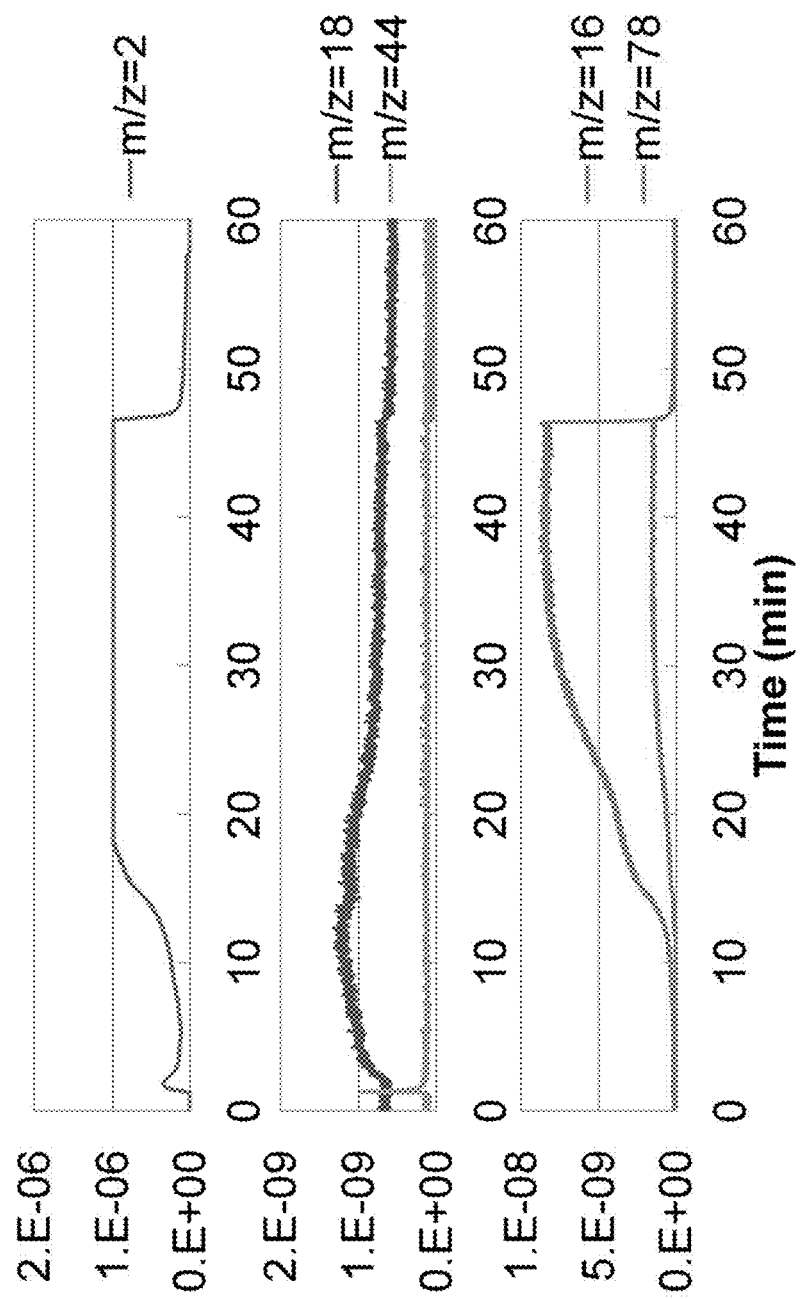
Figure 2E:
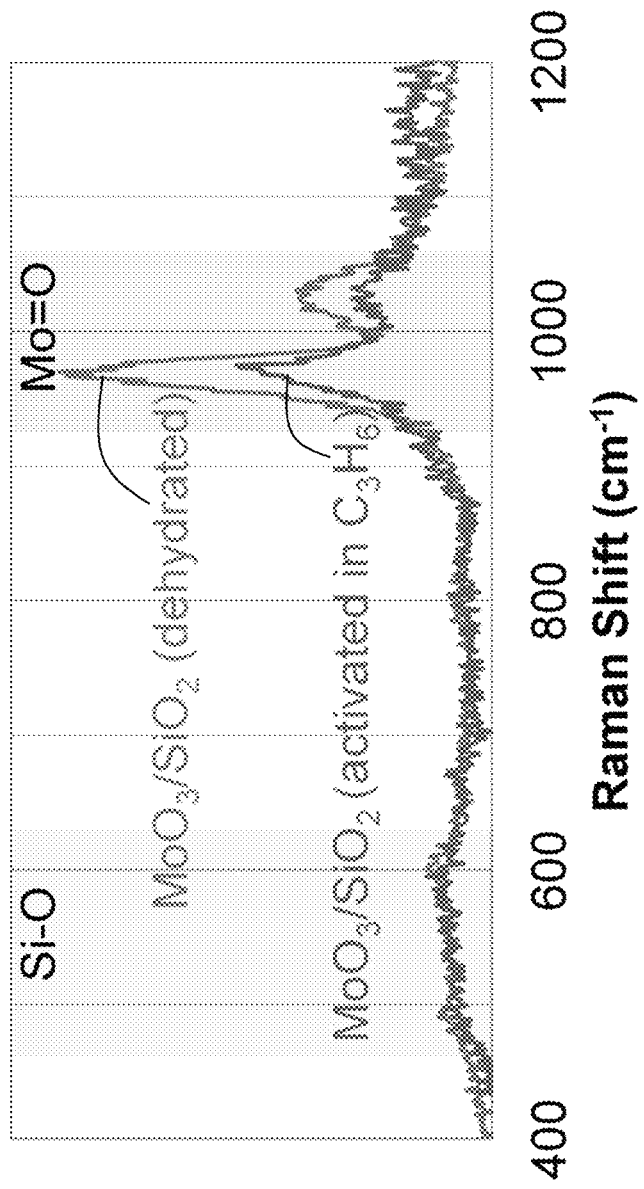
Figure 2F:
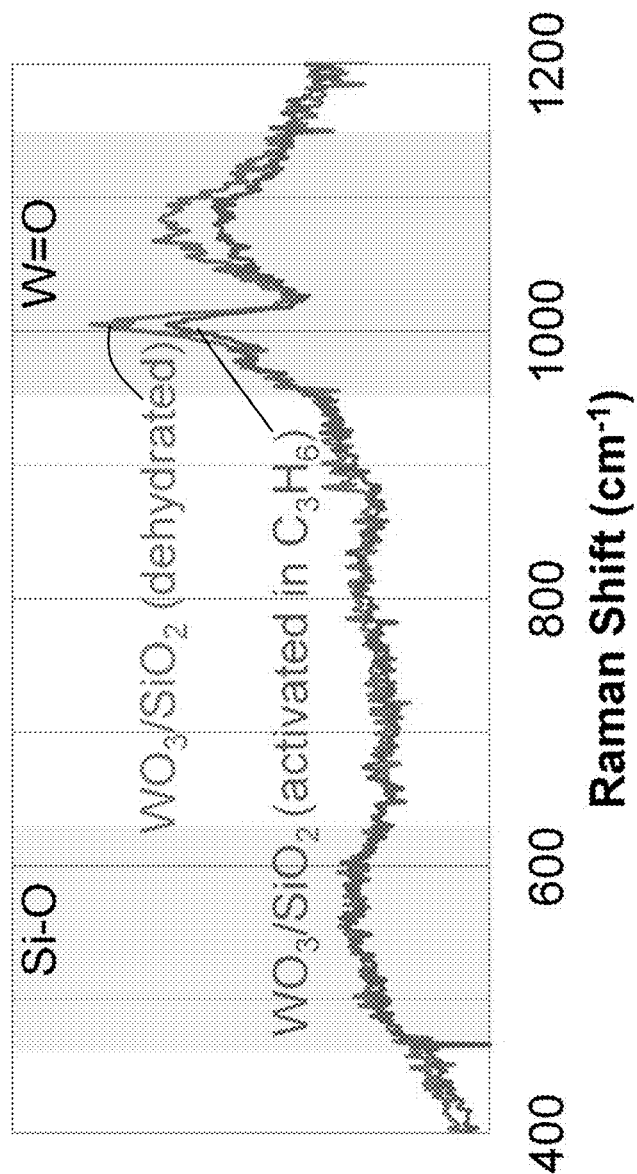
Figure 2G:
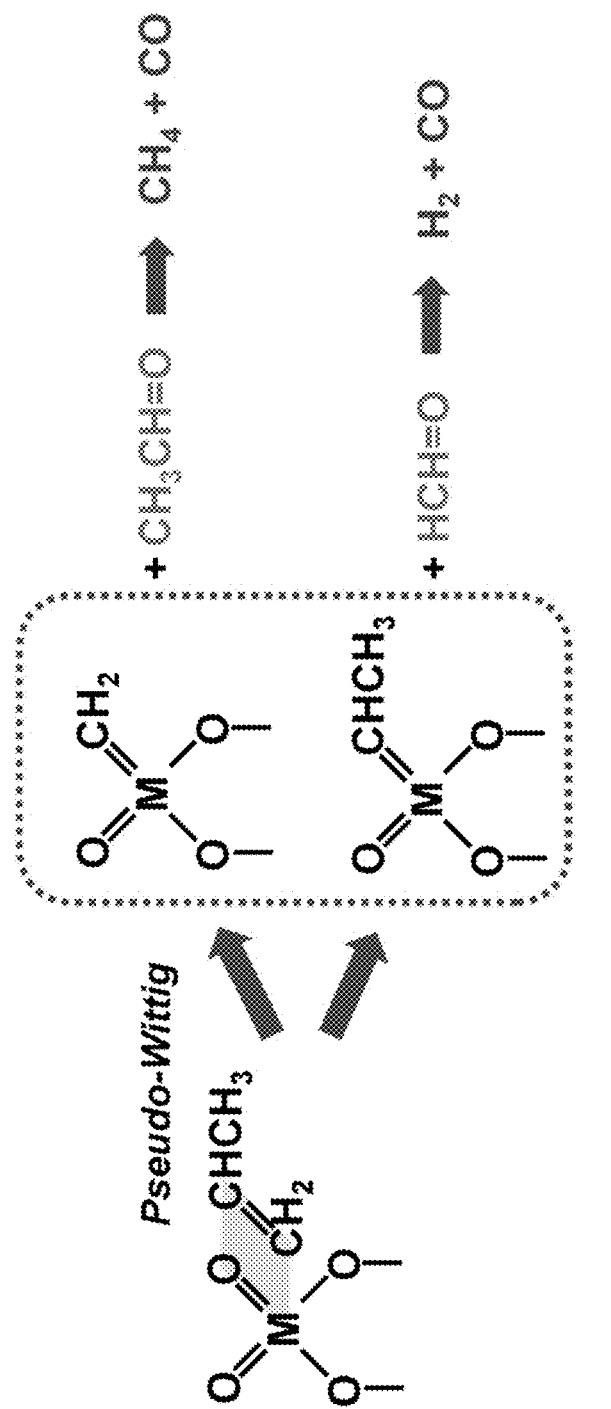

It is likely that the activation $MoO_3$/$SiO_2$ and $WO_3$/$SiO_2$ involve a so-called pseudo-Wittig reaction, which converts Mo=O and W=O into Mo=CHR and W=CHR (R=H, $CH_3$), releasing unstable aldehydes which quickly decompose into CO, $CH_4$ and $H_2$. CO and $H_2$ could further evolve to $CO_2$ and $H_2O$ via surface redox reactions at the early stage of the activation process. The formation of benzene and excess amount of ethylene should be from dehydroaromatization and cracking of $C_3H_6$, respectively. As shown in FIGS. 2E and 2F, the decrease of Mo=O and W=O in the activation process is confirmed by UV-Raman spectroscopy.

Figure 5:
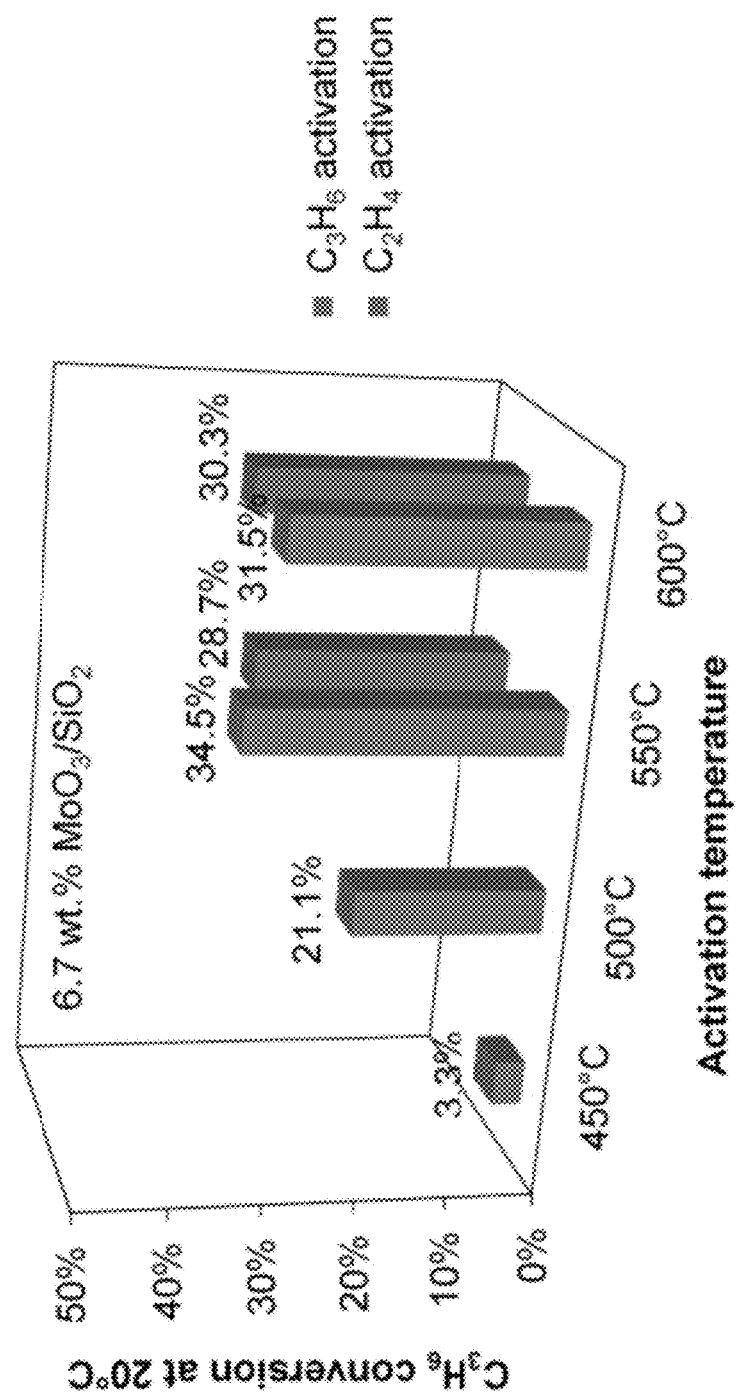
FIG. 5 shows the propylene metathesis activity of $MoO_3$/$SiO_2$ activated in $C_3H_6$/$N_2$ and $C_2H_4$/$N_2$ at different temperatures. Prior to activation, 200 mg of catalyst was calcined in air at 550° C. for 30 min, then purged with $N_2$ at 550° C. for 30 min. The catalyst was activated in $C_3H_6$:$N_2$=4 sccm:96 sccm at the target temperature for 30 min; purged with $N_2$ at the same temperature for 10 min; cooled down to 20° C. in $N_2$; switched to $C_3H_6$:$N_2$=40 sccm:5 sccm.
Figure 6:
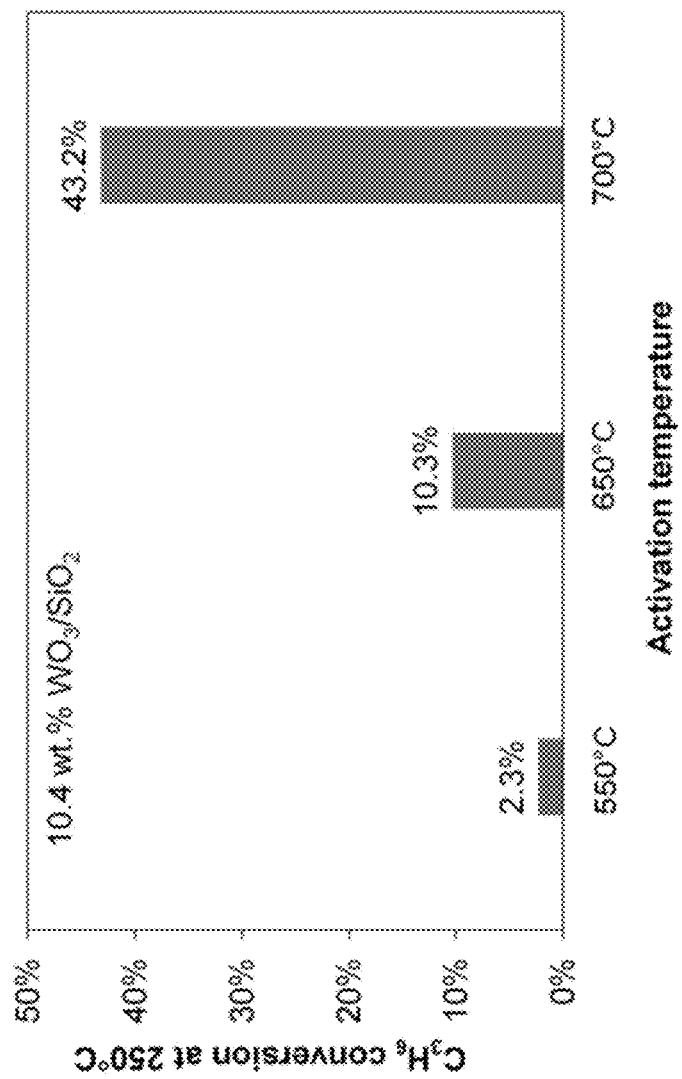
FIG. 6 shows the propylene metathesis activity of $WO_3$/$SiO_2$ activated in $C_3H_6$/$N_2$ at different temperatures. Prior to activation, 200 mg of catalyst was calcined in air at 550° C. for 30 min, then purged with $N_2$ at 550° C. for 30 min. The catalyst was activated in $C_3H_6$:$N_2$=4 sccm:96 sccm at the target temperature for 30 min; purged with $N_2$ at the same temperature for 10 min; cooled down to 250° C. in $N_2$; switched to $C_3H_6$:$N_2$=40 sccm:5 sccm.

Experiments showed that the catalytic activity is sensitive to the pretreatment temperature (FIGS. 5 and 6). In order to remove oxygen atoms and give rise to high activity, the activation temperature is desirably close to 550° C. for $MoO_x$/$SiO_2$ and 700 ° C. for $WO_x$/$SiO_2$.

Figure 7:
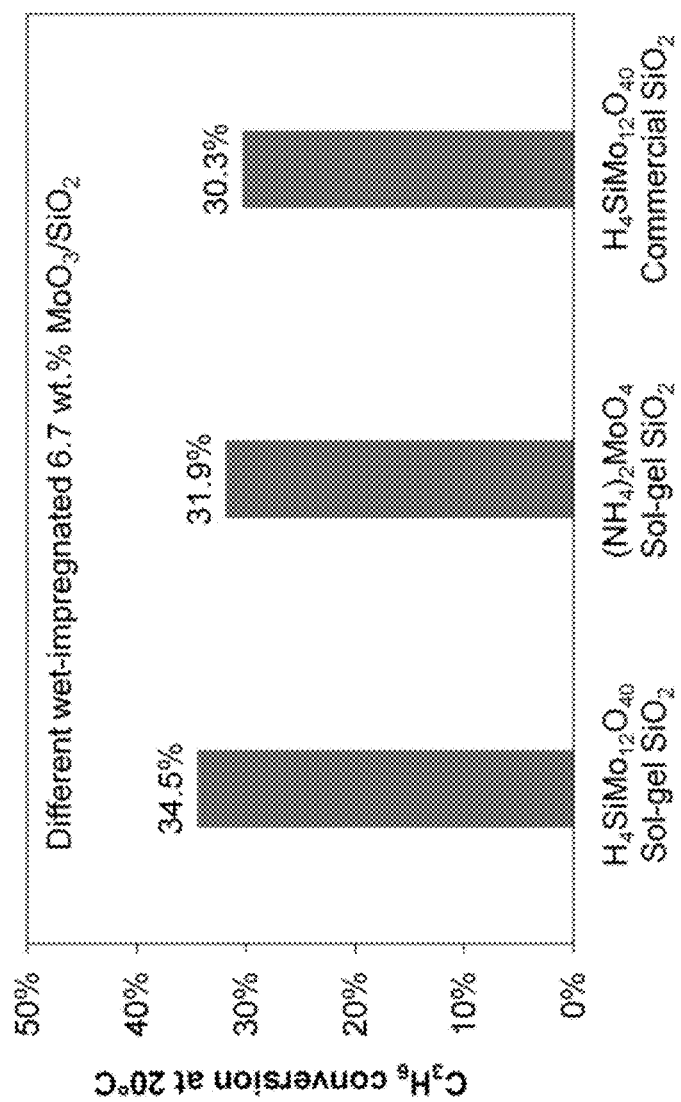
FIG. 7 shows the propylene metathesis activity of $MoO_3$/$SiO_2$ prepared from different Mo precursors and $SiO_2$ supports. Prior to activation, 200 mg of catalyst was calcined in air at 550° C. for 30 min, then purged with $N_2$ at 550° C. for 30 min. The catalyst was activated in $C_3H_6$:$N_2$=4 sccm:96 sccm at 550° C. for 30 min; purged with $N_2$ at 550° C. for 10 min; cooled down to 20° C. in $N_2$; switched to $C_3H_6$:$N_2$=40 sccm:5 sccm.

This activation mechanism suggests that other olefins might do similar job to propylene in the activation process. Indeed, when ethylene was used instead of propylene for the activation of $MoO_3$/$SiO_2$, similar catalytic performance was achieved for propylene metathesis at room temperature (FIG. 5). Moreover, the generality of the approach was established by using different $MoO_3$ precursors or $SiO_2$ supports for the wet-impregnation synthesis of $MoO_3$/$SiO_2$, both of which showed similarly high catalytic performance (FIG. 7).

In order to explain the high activity of the pretreated $MoO_3$/$SiO_2$ and $WO_3$/$SiO_2$, the amount of active sites was counted by isotope tracing. The experimental procedure was as follows: 200 mg of 7 wt. % $MoO_3$/$SiO_2$, calcined in air (50 sccm) at 550° C. for 30 min, then purged with $N_2$ (100 sccm) at 550° C. for 30 min; activated in $C_3H_6$:$N_2$=4 sccm:96 sccm at 550° C. for 30 min, then purged with $N_2$ (100 sccm) at 550° C. for 10 min, cooled down to room temperature under $N_2$ (100 sccm); switched to $C_3H_6$:$N_2$=40 sccm:5 sccm for 10 min, then purged with $N_2$ (100 sccm) for 20 min; switched to $C_2D_4$:$N_2$=0.5 sccm:14.5 sccm for 10 min, then purged with $N_2$ (100 sccm) for 20 min. Thus, after the activated $MoO_3$/$SiO_2$ catalyst reached a steady state in propylene metathesis at room temperature, the system was thoroughly purged with nitrogen, followed by the dosing of $CD_2$=$CD_2$. Mass/charge ratio of 43 and 44, which are assigned to $CD_2$=$CHCH_3$, were monitored during the dosing of $CD_2$=$CD_2$. The peaks of m/z=43 and 44 represent 2% of Mo=$CHCH_3$ in the total amount of Mo sites (data not shown). Suppose the amount of Mo=$CH_2$ and Mo=$CHCH_3$ are equal when propylene metathesis reaches a steady state, there are only 4% of the total Mo sites are active in propylene metathesis. Such a small percentage of active site is already much higher than most molybdenum oxide based olefin metathesis catalysts (See, K. Amakawa et al., *J. Am. Chem. Soc.* 134, 11462 (2012).) This may in part explain the high activity of the activated catalysts. Knowing the average TOF and the amount of active sites in $MoO_3$/$SiO_2$, it can easily be calculated that the specific TOF of these active sites is $1.5 \times 10^4$/h, and the specific accumulative TON is $2.8 \times 10^5$ in 40 hours. These specific TOF and TON are similar to those well-defined organometallic Mo-based olefin metathesis catalysts. (See, F. Blanc et al., *J. Am. Chem. Soc.* 129, 8434 (2007) and F. Blanc et al., *J. Am. Chem. Soc.* 129, 1044 (2007).

UV-Raman spectra suggest that almost half of the Mo=O disappeared after the activation process. Clearly most of the Mo sites are spectators in olefin metathesis. This can be attributed to the heterogeneity of the Mo site structure on the $SiO_2$ support surface. STEM-HAADF images of the $MoO_3$/$SiO_2$ and $WO_3$/$SiO_2$ were obtained and show that $MoO_3$ and $WO_3$ are well dispersed on the $SiO_2$ surface in the form of very small clusters (data not shown). These clusters fall in a wide size range from ~0.5 nm to ~2 nm, containing $10^0$ to $10^2$ Mo or W atoms. No long range ordering has been observed in these clusters, indicating the amorphous nature of their structures. DFT calculations by Handzlik show that the activity of Mo site on $SiO_2$ varies significantly with its local coordination structure. However, these calculations were performed on single-site $MoO_x$ supported on a crystalline $SiO_2$ surface. Considering the amorphous nature of the $MoO_3$ and $WO_3$ clusters as well as the $SiO_2$ support, the situation is even more complex. Among the large variety of Mo and W site structures, it is not surprising that only a few percent of them are active in olefin metathesis at low temperatures.

As shown in FIGS. 1A-1F, $MoO_3$/$SiO_2$ and $WO_3$/$SiO_2$ gradually deactivates with the reaction time. This should be attributed to either the loss of accessibility or the structure transformation of the catalytic sites. Temperature programmed oxidation experiments show that the carbon deposition on the freshly activated catalyst and the spent catalyst after long term tests are identical (data not shown). The experimental procedure for Coke quantification via temperature-programmed oxidation (TPO) was as follows: 100 mg of 7 wt. % $MoO_3$/$SiO_2$, 200-550° C., ramp rate of 2.5° C./min, dwelt at 550° C. for 60 min, air=20 sccm. The first TPO experiment was performed after the propylene activation process. The second and third ones were performed after a long term propylene metathesis reaction. The reactor was purged with $N_2$ (100 sccm) for 20 min prior to the TPO process. Activation conditions were as follows: calcined in air (50 sccm) at 550° C. for 30 min, then purged with $N_2$ (100 sccm) at 550° C. for 30 min; activated in $C_3H_6$:$N_2$=4 sccm:96 sccm at 550° C. for 30 min, then purged with $N_2$ (100 sccm) at 550° C. for 10 min, cooled down to room temperature under $N_2$ (100 sccm); switched to $C_3H_6$:$N_2$=40 sccm:5 sccm. This ruled out the possibility of the blockage of catalytic sites by coking or oligomerization being the main reason of $MoO_3$/$SiO_2$ deactivation.

Temperature-programmed propylene metathesis reactions over propylene activated $MoO_3$/$SiO_2$ were conducted using staged temperature ramping and continuous temperature ramping (50-550° C., 1° C./min). The experimental procedure was as follows: 200 mg of 7 wt. % $MoO_3$/$SiO_2$, calcined in air (50 sccm) at 550° C. for 30 min, then purged with $N_2$ (100 sccm) at 550° C. for 30 min; activated in $C_3H_6:N_2$=4 sccm:96 sccm at 550° C. for 30 min, then purged with $N_2$ (100 sccm) at 550° C. for 10 min, cooled down to room temperature under $N_2$ (100 sccm); switched to $C_3H_6$:$N_2$=40 sccm:5 sccm. Both continuous and staged TPRx of propylene metathesis over the activated $MoO_3/SiO_2$ show that the deactivation rate becomes faster when the reaction temperature is increased from 20° C. to 100° C. (data not shown). The activity keeps decreasing with T until it reaches a minimum at approximately 140° C., and then rises up again.

This type of TPRx suggests that the low temperature deactivation is very likely reversible. Thus, the regeneration of deactivated $MoO_3/SiO_2$ catalyst via $N_2$ purging at elevated temperatures was studied for catalyst: deactivated under propylene metathesis at 100° C.; catalyst deactivated by air poisoning at room temperature; and catalyst deactivated by $H_2O$ poisoning at room temperature. The experimental procedure was as follows: 200 mg of 7 wt. % $MoO_3/SiO_2$, calcined in air (50 sccm) at 550° C. for 30 min, then purged with $N_2$ (100 sccm) at 550° C. for 30 min; activated in $C_3H_6:N_2$=4 sccm:96 sccm at 550° C. for 30 min, then purged with $N_2$ (100 sccm) at 550° C. for 10 min, cooled down to room temperature under $N_2$ (100 sccm); switched to $C_3H_6:N_2$=40 sccm:5 sccm. The reactor was purged with $N_2$ (100 sccm) at room temperature for 20 min prior to poisoning (air poisoning: air=50 sccm, 20° C., 3 min; $H_2O$ poisoning: $N_2$=20 sccm, $H_2O$ vapor 20° C., 10 min), resuming metathesis reaction, and temperature-programmed desorption. In fact, when the low temperature deactivated $MoO_3/SiO_2$ catalyst was purged with $N_2$ at a temperature above 300° C. and then cooled down to room temperature, the propylene metathesis activity was fully recovered by $N_2$ purging at 300° C. and 550° C. (data not shown). However after the dose of $O_2$ or $H_2O$, the propylene metathesis activity of $MoO_3/SiO_2$ significantly dropped about 90%, and the activity was not recovered by $N_2$ purging at 300° C. The activity of $O_2$ poisoned $MoO_3/SiO_2$ was fully recovered by $N_2$ purging at 550° C. At the same condition, the activity of $H_2O$ poisoned $MoO_3/SiO_2$ was only partially recovered. These experiments clearly ruled out the possibility of $O_2$ and $H_2O$ poisoning being the main reason of $MoO_3/SiO_2$ deactivation under the metathesis conditions.

Figure 3A:
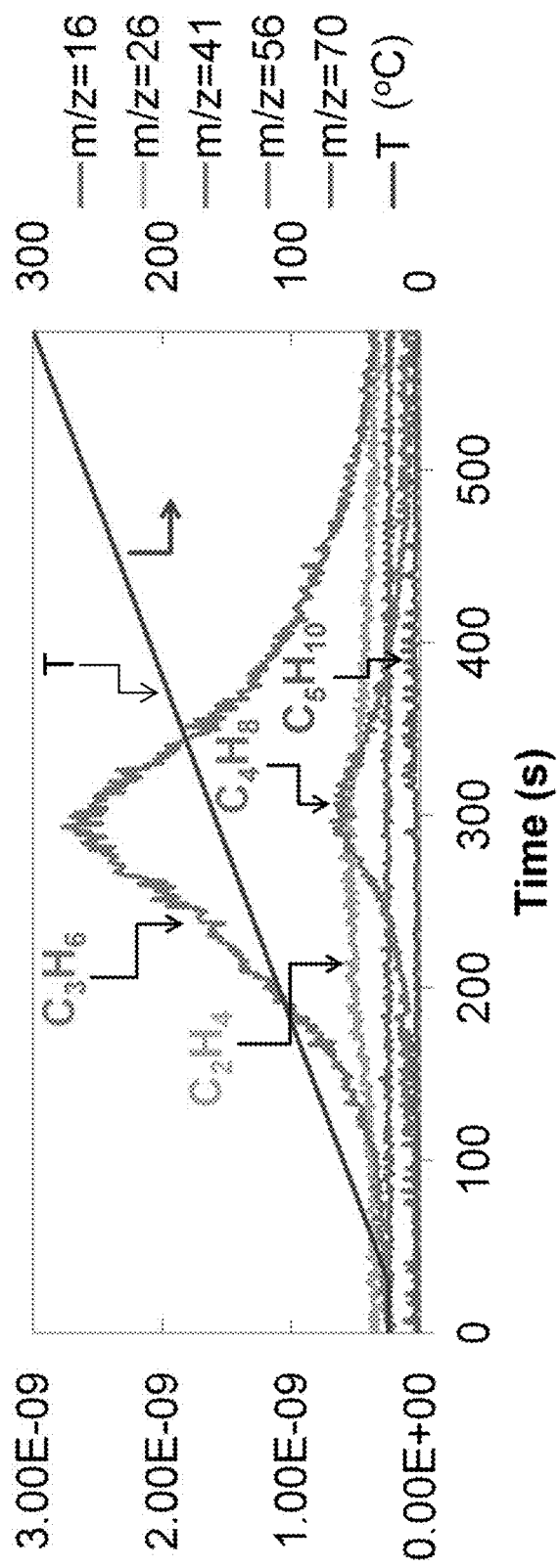
FIGS. 3A-3D further relate to the regeneration mechanisms.
Figure 3B:
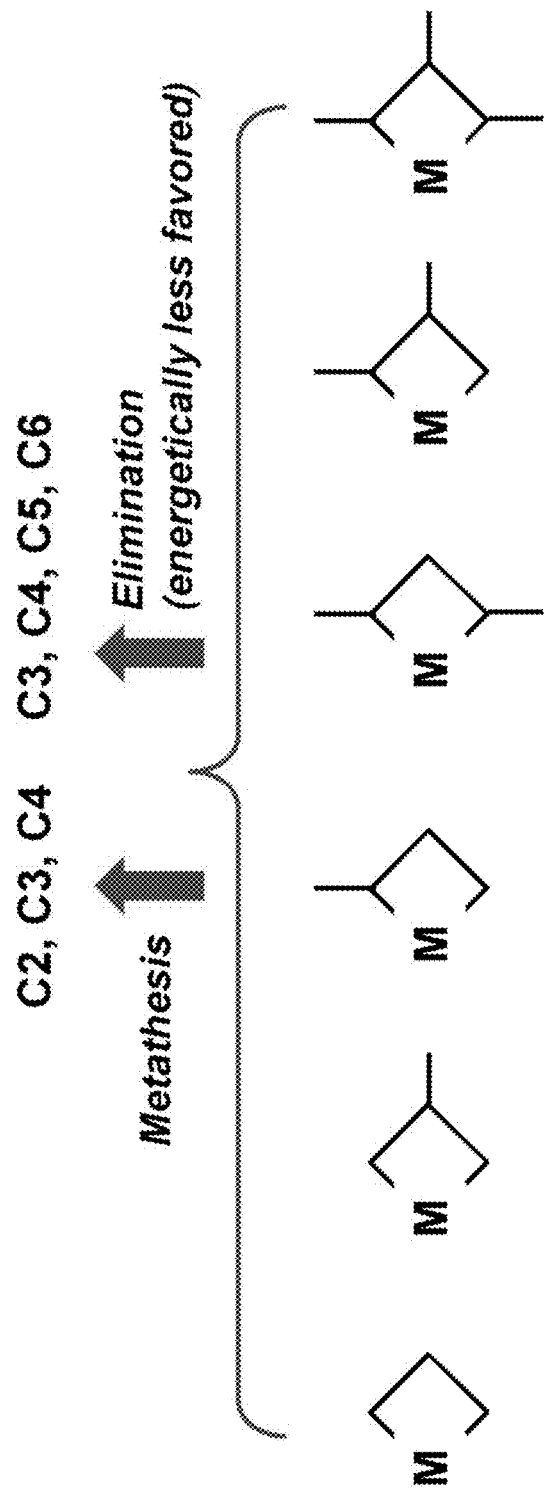
Figure 3C:
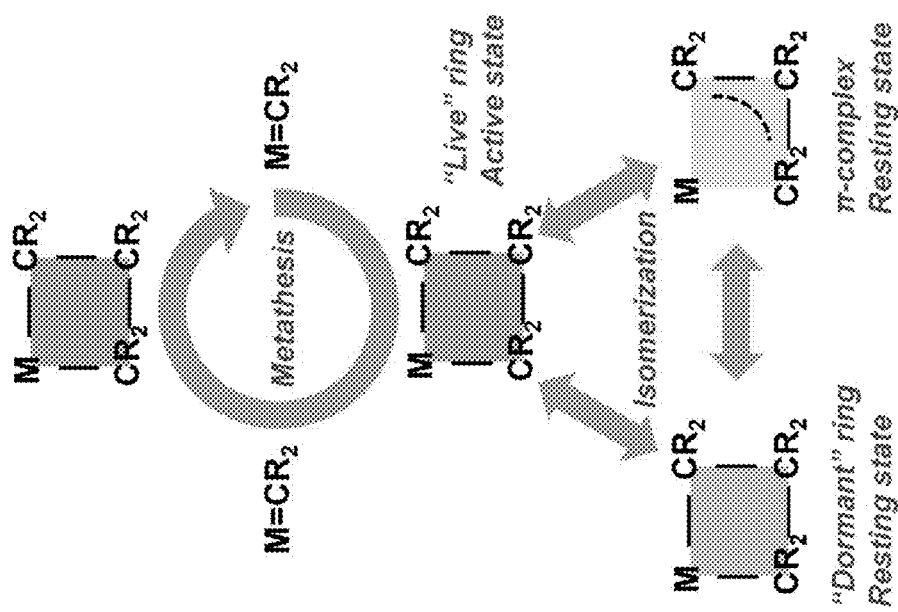
Figure 3D:
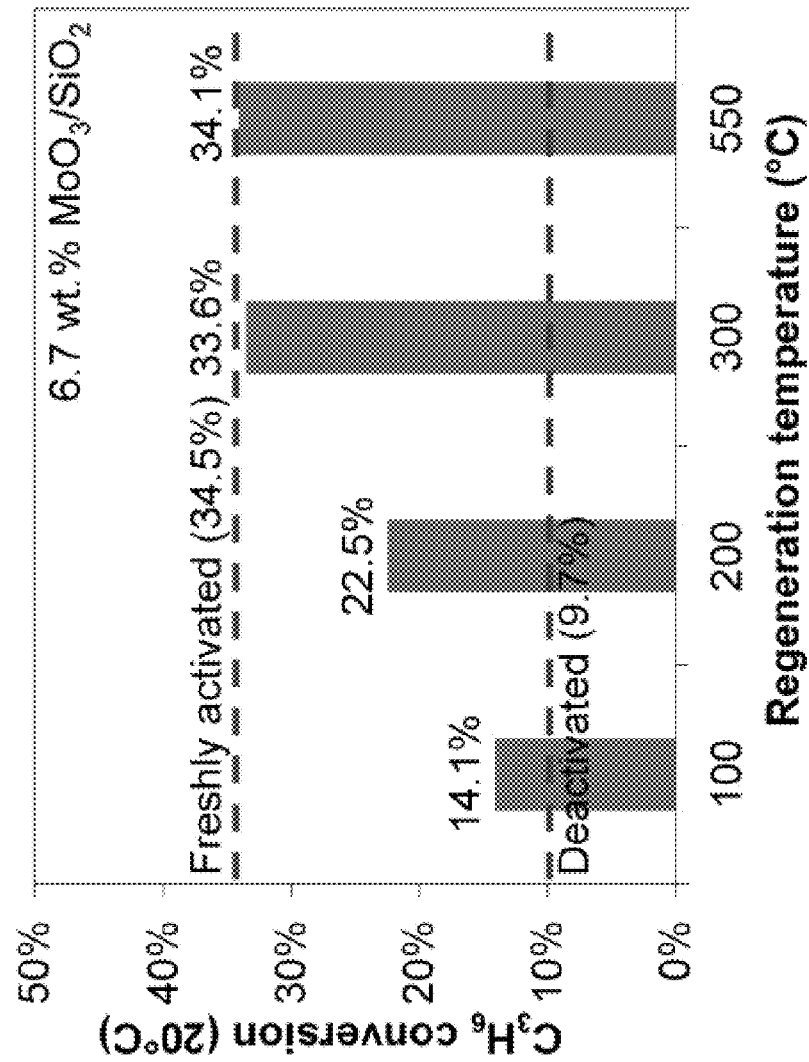

In order to gain more in-depth understanding of the deactivation and regeneration of the $MoO_3/SiO_2$ catalyst, MS was used to monitor the temperature-programmed desorption process of the low temperature deactivation $MoO_3/SiO_2$ catalyst. As shown in FIG. 3A, ethylene (m/z=26), propylene (m/z=41), butene (m/z=56), and pentene (m/z=70) signals were observed sequentially when temperature ramped up. Desorption of all of these species were completed before 300° C. These desorbed species should be attributed to the decomposition of the metallacyclobutanes with different branches remained on the catalyst surface (FIG. 3B). That desorption of these species is responsible for the regeneration of active sites at a regeneration temperature as low as 300° C. was confirmed in the experiments (FIG. 3D). Regeneration at 200° C. and 100° C. led to only partial recovery of activity.

Data shown above suggest that the low temperature deactivation of $MoO_3/SiO_2$ in propylene metathesis follows an intrinsic mechanism. (See, J. C. Mol, P. W. N. M. van Leeuwen, in *Handbook of Heterogeneous Catalysis*. (2008), vol. 14, pp. 3240-3256 and A. Salameh et al., *J. Catal.* 253, 180 (2008). In addition to the Hérisson-Chauvin catalytic cycle, resting states of the metallacyclobutanes have been suggested by experimental and theoretical work. DFT calculations show that the metallacyclobutanes are able to change their configurations during the reaction, and each configuration has different energy state, therefore lead to different energy barrier in metathesis reaction. The metallacyclobutanes with trigonal bipyramidal geometry are more active in metathesis, while these with square pyramidal geometry are energetically more stable and therefore less active in metathesis. Another resting state, π-complex, has also been suggested. The populations of these structures vary with reaction time and temperature. Eventually most of the structures are converted to energetically more stable, but catalytically less active structures, and thereby the catalyst is deactivated. Upon inert gas purging at elevated temperatures, all types of the metallacyclobutanes and π-complexes decompose and restore the original active surface structures, and the catalyst is regenerated. Given the general nature of the deactivation mechanism, the regeneration pathway described herein may be universal for metal oxide based olefin metathesis catalysts.

Identification and characterization of catalytic active sites are prerequisites for an atomic-level understanding of the catalytic mechanism and rational design of high-performance heterogeneous catalysts. To this end, the number of active sites of the pretreated $MoO_3/SiO_2$ were counted by isotope tracing as detailed above. In brief, after the activated $MoO_3/SiO_2$ catalyst reached a steady state in propylene metathesis at room temperature, the system was thoroughly purged with nitrogen, followed by dosing with $^{13}CH_2=^{13}CH_2$. The formation of $^{13}CH_2=CH_2$ and $^{13}CH_2=CHCH_3$, originating from Mo=$CH_2$ and Mo=$CHCH_3$, respectively, was monitored by MS. A series of $MoO_3/SiO_2$ catalysts with different loadings were tested and the counting results are given in FIG. 8A and the Table below. The fraction of active Mo on the 6.7 wt. % $MoO_3/SiO_2$ dramatically increases from close to zero (negligible without a high temperature propylene pretreatment) to 4.2% after a high temperature propylene pretreatment. The fraction of active Mo increases as the loading of $MoO_3$ decreases and is maximized at 11% on the 1.4 wt. % $MoO_3/SiO_2$ material. The fraction of active Mo obtained by the present procedure is 10-fold higher than most supported $MoO_3$ catalysts (K. Amakawa et al., *J. Am. Chem. Soc.* 134, 11462 (2012)). This explains, in part, the high activity of high temperature, olefin-pretreated catalysts.

TABLE

Results of active site counting by $^{13}CH_2=^{13}CH_2$ tracing.

| $MoO_3$ loading (wt. %) | Mo coverage (per nm$^2$) | Sample weight (mg) | $^{13}CH_2=^{12}CH_2$ (mmol) | $^{13}CH_2=^{12}CH^{12}CH_3$ (mmol) | Fraction of active Mo | Active Mo density (per nm$^2$) |
|---|---|---|---|---|---|---|
| 1.4% | 0.059 | 300 | 0.00067 | 0.00256 | 10.9% | 0.006 |
| 2.8% | 0.14 | 200 | 0.00108 | 0.00228 | 8.6% | 0.012 |

TABLE-continued

Results of active site counting by $^{13}CH_2=^{13}CH_2$ tracing.

| MoO$_3$ loading (wt. %) | Mo coverage (per nm$^2$) | Sample weight (mg) | $^{13}CH_2=^{12}CH_2$ (mmol) | $^{13}CH_2=^{12}CH^{12}CH_3$ (mmol) | Fraction of active Mo | Active Mo density (per nm$^2$) |
|---|---|---|---|---|---|---|
| 6.7% | 0.35 | 200 | 0.00139 | 0.00250 | 4.2% | 0.014 |
| 12.6% | 0.80 | 200 | 0.00172 | 0.00382 | 3.2% | 0.022 |
| 20.1% | 2.6 | 200 | 0.00180 | 0.00344 | 1.9% | 0.039 |
| 30.2% | 8.5 | 200 | 0.00112 | 0.00177 | 0.7% | 0.041 |
| *6.7% | 0.35 | 200 | 0 | 0 | 0 | 0 |

*Pretreated by 550° C. calcination and nitrogen purge but without high temperature propylene pretreatment.
Note:
The amount of $^{13}CH_2=CHCH_3$ is always greater than that of $^{13}CH_2=CH_2$, indicating a higher activity of Mo=CH$_2$ compared to Mo=CHCH$_3$. This suggests that a lot of active site counting results reported in the literatures were actually overestimated, as they only counted Mo=CHCH$_3$ and assumed that the amounts of Mo=CH$_2$ and Mo=CHCH$_3$ were equal (J. Handzlik, J. Ogonowski, *Catal. Lett.* 88, 119 (2003); K. Amakawa et al., *J. Am. Chem. Soc.* 134, 11462 (2012)).

The surface concentration of active sites was calculated by normalizing the total number of active sites to the specific surface area of the catalyst, which was measured by N$_2$ sorption. As shown in FIG. 8A, the surface concentration of active sites increases with MoO$_3$ loading and levels off beyond a loading of ca. 20 wt. %. Infrared spectroscopy of MoO$_3$/SiO$_2$ showed that the silanols are almost completely consumed at 20 wt. % (FIG. 8B), implying that the molybdate species have saturated the SiO$_2$ surface at this loading. The formation of micron-sized MoO$_3$ crystals at 20 wt. % was confirmed by X-ray diffraction and electron microscopy. UV-Vis diffuse reflectance spectra showed that the absorption band edge of the MoO$_3$/SiO$_2$ catalysts red-shifts with the MoO$_3$ loading, indicating an increased average degree of polymerization of the molybdate species. Unfortunately, all the techniques shown above give only sample-averaged information. In order to indentify the active site structure for olefin metathesis, a site-specific technique to characterize different molybdate species is needed.

Raman spectroscopy is powerful in probing the structures of supported metal oxides. Great success has been achieved in indentifying the catalytically active site structures using this technique, including WO$_x$/ZrO$_2$ in alkane isomerization, MoO$_x$/zeolite in methane dehydroaromatization, etc. Compared to normal Raman spectroscopy, resonance Raman spectroscopy can provide much higher sensitivity and selectivity in detecting surface metal oxides despite their low concentrations. As shown in FIG. 8C, several bands appear in the region 950-1100 cm$^{-1}$, belonging to the Mo=O stretching vibration. In general, bands above 990 cm$^{-1}$ are assigned to Mo=O monooxo species. According to DFT calculations, Mo=O monooxo sites do not contribute to the metathesis activity because they form rather stable surface species. The bands below 990 cm$^{-1}$ are assigned to Mo(=O)$_2$ dioxo species. The dramatic change in the relative intensities of the bands below and above 990 cm$^{-1}$ on UV resonance Raman (244 nm) and visible Raman (488 nm) spectra of high MoO$_3$ loading samples suggests that the bands below 990 cm$^{-1}$ were resonance enhanced by more than 100-fold. Since asymmetric modes generally cannot be resonance enhanced, which should be invisible on a UV resonance Raman spectrum, the two bands at 983±4 cm$^{-1}$ and 969±4 cm$^{-1}$ should be assigned to the symmetric stretching modes of two distinct Mo(=O)$_2$ dioxo species, monomeric and polymeric, respectively (FIG. 8C).

The peak areas of the Raman bands at 983±4 cm$^{-1}$ and 969±4 cm$^{-1}$ are normalized to the specific surface area of each MoO$_3$/SiO$_2$ sample and were plotted against the loading in FIG. 8D. As shown in FIGS. 8A and 8D, the area of the 983±4 cm$^{-1}$ band correlates well with the trend of active site surface concentration, pointing to the conclusion that the active sites of MoO$_3$/SiO$_2$ in olefin metathesis are monomeric Mo(=O)$_2$ dioxo species. The monomeric nature of the metathesis active sites in supported MoO$_x$ catalysts has been previously suggested based on the relatively high activity of highly dispersed MoO$_x$ synthesized through grafting, flame synthesis, and aerosol synthesis; however, this is the first time clear spectroscopic evidence has been obtained showing a positive correlation between the surface concentration of active sites and monomeric Mo(=O)$_2$ dioxo species.

Aberration-corrected high-angle annular dark-field (HAADF) imaging studies confirmed the monomeric nature of the active site on MoO$_3$/SiO$_2$ catalysts. A mixture of monomeric, oligomeric, and clustered molybdates were observed throughout a broad range of loadings, and the population of all species increased with loading. Remarkably, clusters always appeared to be the dominant surface species even at relatively low MoO$_3$ loadings, since silica supported transition metal oxides with low loadings were previously believed to be mostly monomeric species. On the other hand, this agrees well with the Raman spectroscopic evidence that monomeric Mo(=O)$_2$ dioxo species are the active sites and represent a small fraction of the surface Mo species. Based on the spectroscopy and electron microscopy studies, successful syntheses of predominantly monomeric Mo(=O)$_2$ dioxo species would greatly improve the olefin metathesis activity for supported MoO$_x$ catalysts. Similar conclusions may be made for WO$_x$ and ReO$_x$ based olefin metathesis catalysts.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the subject matter has been presented for purposes of illustration and of description. It is not intended to be exhaustive or to limit the subject matter to the precise form disclosed, and modifications and variations are possible in light of the above teachings or may be acquired from practice of the subject matter. The embodiments were chosen and described in order to explain the principles of the subject matter and as practical applications of the subject matter to enable one skilled in the art to utilize the subject matter in various embodiments and with various modifications as suited to the particular use contemplated. It is intended that the scope of the subject matter be defined by the claims appended hereto and their equivalents.

What is claimed is:

1. A method comprising:
(a) exposing a supported heterogeneous metathesis catalyst comprising a support material and transition metal active groups dispersed on the support material to a first olefin compound for an activation time at an activation temperature, thereby providing an activated supported heterogeneous metathesis catalyst;
(b) exposing the activated supported heterogeneous metathesis catalyst to a reactant capable of undergoing a metathesis reaction for a reaction time at a reaction temperature to produce metathesis products, thereby providing a deactivated supported heterogeneous metathesis catalyst; and
(c) exposing the deactivated supported heterogeneous metathesis catalyst to a regenerating compound for a regeneration time at a regeneration temperature, thereby providing a regenerated supported heterogeneous metathesis catalyst, wherein the activity of the regenerated supported heterogeneous metathesis catalyst is substantially the same or greater than the activity of the activated supported heterogeneous metathesis catalyst prior to deactivation,
wherein the activation temperature is greater than the reaction temperature,
wherein the regenerating compound is provided as an inert gas atmosphere substantially free of oxygen or air,
and further wherein regeneration to achieve substantially the same or greater activity as compared to the activated supported heterogeneous metathesis catalyst prior to deactivation is accomplished without exposing the deactivated supported heterogeneous metathesis catalyst to another olefin compound and without exposing the deactivated supported heterogeneous metathesis catalyst to oxygen.

2. The method of claim 1, wherein the regeneration temperature is at least about 200° C.

3. The method of claim 1, wherein the method comprises repeating steps (b) and (c) at least one additional time.

4. The method of claim 1, wherein the method comprises repeating steps (b) and (c) at least twice.

5. The method of claim 1, wherein the transition metal active groups are transition metal oxide active groups.

6. The method of claim 5, wherein the transition metal oxide active groups are tungsten oxide active groups, molybdenum oxide active groups, rhenium oxide active groups, ruthenium oxide active groups, tantalum oxide active groups or niobium oxide active groups.

7. The method of claim 5, wherein the transition metal oxide active groups are $WO_3$ active groups, $MoO_3$ active groups, $Re_2O_7$ active groups, $RuO_2$ active groups, $Ta_2O_5$ active groups, or $Nb_2O_5$ active groups.

8. The method of claim 1, wherein the activation temperature is at least about 200° C.

9. The method of claim 1, wherein the exposure in step (a) is accomplished by exposing the supported heterogeneous metathesis catalyst at a first activation temperature which is ramped to a second activation temperature at a temperature ramping rate during the activation time.

10. The method of claim 1, wherein the exposure in step (a) is accomplished by flowing a gas mixture comprising the first olefin compound and a carrier over the supported heterogeneous metathesis catalyst.

11. The method of claim 1, wherein between steps (a) and (b), the method further comprises exposing the activated supported heterogeneous metathesis catalyst to an inert gas for a purging time at a purging temperature, wherein the purging temperature is substantially the same as the activation temperature.

12. The method of claim 1, wherein between steps (a) and (b), the method further comprises exposing the activated supported heterogeneous metathesis catalyst to an inert gas for a purging time at a purging temperature, wherein the purging temperature is substantially the same as the activation temperature or greater, and further wherein the regeneration temperature is substantially the same as the activation temperature or greater.

13. The method of claim 12, wherein the purging temperature and the regeneration temperature are each substantially the same as the activation temperature.

14. The method of claim 13, wherein the activation temperature is at least about 200° C.

15. A method of regenerating a deactivated supported heterogeneous metathesis catalyst, the method comprising exposing a deactivated supported heterogeneous metathesis catalyst comprising a support material and transition metal active groups dispersed on the support material to an inert gas atmosphere substantially free of oxygen or air for a regeneration time at a regeneration temperature, thereby providing a regenerated supported heterogeneous metathesis catalyst, wherein the activity of the regenerated supported heterogeneous metathesis catalyst is substantially the same or greater than the activity of the supported heterogeneous metathesis catalyst prior to deactivation,
and further wherein regeneration to achieve substantially the same or greater activity as compared to the supported heterogeneous metathesis catalyst prior to deactivation is accomplished without exposing the deactivated supported heterogeneous metathesis catalyst to an olefin compound and without exposing the deactivated supported heterogeneous metathesis catalyst to oxygen.

16. The method of claim 15, wherein the transition metal active groups are transition metal oxide active groups.

17. The method of claim 15, wherein the regeneration time is about 10 minutes or less.

18. A method comprising:
(a) exposing a supported heterogeneous metathesis catalyst comprising a support material and transition metal active groups dispersed on the support material to a first olefin compound for an activation time at an activation temperature of at least about 400° C., thereby providing an activated supported heterogeneous metathesis catalyst;
(b) exposing the activated supported heterogeneous metathesis catalyst to a reactant capable of undergoing a metathesis reaction for a reaction time at a reaction temperature of no more than about 250° C. to produce metathesis products, thereby providing a deactivated supported heterogeneous metathesis catalyst; and
(c) exposing the deactivated supported heterogeneous metathesis catalyst to a regenerating compound for a regeneration time at a regeneration temperature, thereby providing a regenerated supported heterogeneous metathesis catalyst, wherein the activity of the regenerated supported heterogeneous metathesis catalyst is substantially the same or greater than the activity of the activated supported heterogeneous metathesis catalyst prior to deactivation.

19. The method of claim 18, wherein the first olefin compound is propylene.

20. The method of claim 18, wherein the transition metal active groups are transition metal oxide active groups and further wherein the activity of the regenerated supported heterogeneous metathesis catalyst is characterized by a turnover frequency of at least about $10^3$/h.

* * * * *